US009382322B2

(12) United States Patent
Al-Jamal et al.

(10) Patent No.: US 9,382,322 B2
(45) Date of Patent: Jul. 5, 2016

(54) TISSUE REPAIR BY MODULATION OF BETA-1 INTEGRIN BIOLOGICAL FUNCTION

(75) Inventors: Rehab Al-Jamal, Edinburgh (GB); David James Harrison, Edinburgh (GB)

(73) Assignees: Rehab Al-Jamal (GB); Robert John Naylor (GB)

( * ) Notice: Subject to any disclaimer, the term of this patent is extended or adjusted under 35 U.S.C. 154(b) by 432 days.

(21) Appl. No.: 10/576,274

(22) PCT Filed: Oct. 18, 2004

(86) PCT No.: PCT/GB2004/004406
§ 371 (c)(1),
(2), (4) Date: Oct. 9, 2007

(87) PCT Pub. No.: WO2005/037313
PCT Pub. Date: Apr. 28, 2005

(65) Prior Publication Data
US 2008/0118502 A1    May 22, 2008

(30) Foreign Application Priority Data

Oct. 17, 2003  (GB) .................................. 0324345.8
Jan. 5, 2004   (GB) .................................. 0400079.0

(51) Int. Cl.
*A61K 39/395* (2006.01)
*C07K 16/28* (2006.01)
*A61K 39/00* (2006.01)

(52) U.S. Cl.
CPC ....... *C07K 16/2842* (2013.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 5,567,440 | A * | 10/1996 | Hubbell et al. | ............... 424/484 |
| 6,123,941 | A * | 9/2000 | Bissell et al. | ............... 424/158.1 |
| 6,177,475 | B1 | 1/2001 | Tatarintsev et al. | |
| 6,251,419 | B1 * | 6/2001 | Graber et al. | ................. 424/424 |
| 6,652,856 | B2 * | 11/2003 | Gotwals et al. | ............. 424/133.1 |
| 2003/0109435 | A1 * | 6/2003 | Prenner et al. | .................... 514/12 |
| 2003/0186334 | A1 | 10/2003 | Marcinkiewicz | |
| 2007/0048321 | A1 * | 3/2007 | Gotwals et al. | ............. 424/146.1 |
| 2008/0274482 | A1 | 11/2008 | Johansson et al. | |
| 2009/0061463 | A1 | 3/2009 | Johansson et al. | |

FOREIGN PATENT DOCUMENTS

| | | |
|---|---|---|
| JP | 2008-67616 A2 | 3/2008 |
| WO | 97/25031 | 7/1997 |
| WO | 99/37669 A1 | 7/1999 |
| WO | 00/15175 A2 | 3/2000 |
| WO | WO 01/17544 A1 * | 3/2001 |
| WO | 01/54690 | 8/2001 |
| WO | 03/006893 A2 | 1/2003 |

OTHER PUBLICATIONS

Leu et al. Identification of a novel integrin alpha 6 beta 1 binding site in the angiogenic inducer CCN1 (CYR61).J Biol Chem. Sep. 5, 2003;278(36):33801-8.*
Lin et al. CCN3 (NOV) is a novel angiogenic regulator of the CCN protein family. J Biol Chem. Jun. 27, 2003;278(26):24200-8.*
Zweers et al. Integrin alpha2beta1 is required for regulation of murine wound angiogenesis but is dispensable for reepithelialization. J. Invest. Dermatol. 127:467-479, 2007.*
Chantal Binda. Bypassing immunization in an attempt to develop beta1 specific monoclonal human antibodies from semi-synthetic repertoires. Master Thesis. 1999. p. 1-127.*
Clark RA.Fibronectin matrix deposition and fibronectin receptor expression in healing and normal skin.J Invest Dermatol. Jun. 1990;94(6 Suppl):128S-134S.*
Herard et al. Fibronectin and its alpha 5 beta 1-integrin receptor are involved in the wound-repair process of airway epithelium. Am J Physiol. Nov. 1996;271(5 Pt 1):L726-33.*
Chemicon International, Catalog No. MAB 1965, p. 1 Sep. 23, 2002.*
Al-Jamal and Harrison, Beta 1 integrin in tissue remodelling and repair: From phenomena to concepts. Pharmacology & Therapeutics 120 (2008) 81-101.*
Owens RJ, Young RJ. The genetic engineering of monoclonal antibodies. J Immunol Methods. 168(2):149-165, 1994.*
Corry et al. The FASEB Journal. 2004;18:995-997).*
Chen et al., The angiogenic factors Cyr61 and connective tissue growth factor induce adhesive signaling in primary human skin fibroblasts. J Biol Chem. Mar. 30, 2001;276(13):10443-52.*
Weigel-Kelley KA, Yoder MC, Srivastava A. Alpha5beta1 integrin as a cellular coreceptor for human parvovirus B19: requirement of functional activation of beta1 integrin for viral entry. Blood. Dec. 1, 2003;102(12):3927-33. Epub Aug. 7, 2003.*
Ma et al., Selective Inhibition of Matrix Metalloproteinase Isozymes and in Vivo Protection against Emphysema by Substituted ç-Keto Carboxylic Acids. J. Med. Chem. 2006, 49, 456-458.*
Ni H, Wilkins JA., Localisation of a novel adhesion blocking epitope on the human beta 1 integrin chain. Cell Adhes Commun. Jun. 1998;5(4):257-71.*
Beachy PA et al. Tissue repair and stem cell renewal in carcinogenesis. Nature. Nov. 18, 2004;432(7015):324-31.*
Herrup K et al. Divide and die: cell cycle events as triggers of nerve cell death. J Neurosci. Oct. 20, 2004;24(42):9232-9.*
Luo BH et al. Allosteric beta1 integrin antibodies that stabilize the low affinity state by preventing the swing-out of the hybrid domain. J Biol Chem. Jun. 25, 2004;279(26):27466-71.*

(Continued)

*Primary Examiner* — Maher Haddad
(74) *Attorney, Agent, or Firm* — DLA Piper LLP (US)

(57) ABSTRACT

The present invention methods and novel compounds for facilitating tissue repair and regeneration when the extracellular matrix is damaged. Specifically, binding of the beta 1 integrin is shown to provide a modulation of its functional activity resulting in up regulation of extracellular matrix anabolism. The invention therefore provides a method and novel compounds which can facilitate tissue regeneration in many systems such as the lung, skin, liver and bone. In particular, the binding of the JB1a antibody to a site of amino acid residues 82 to 87 of the mature beta 1 integrin is shown to be particularly effective in mediating the described tissue repair effect.

9 Claims, 30 Drawing Sheets

(56) References Cited

OTHER PUBLICATIONS

Figure 1:
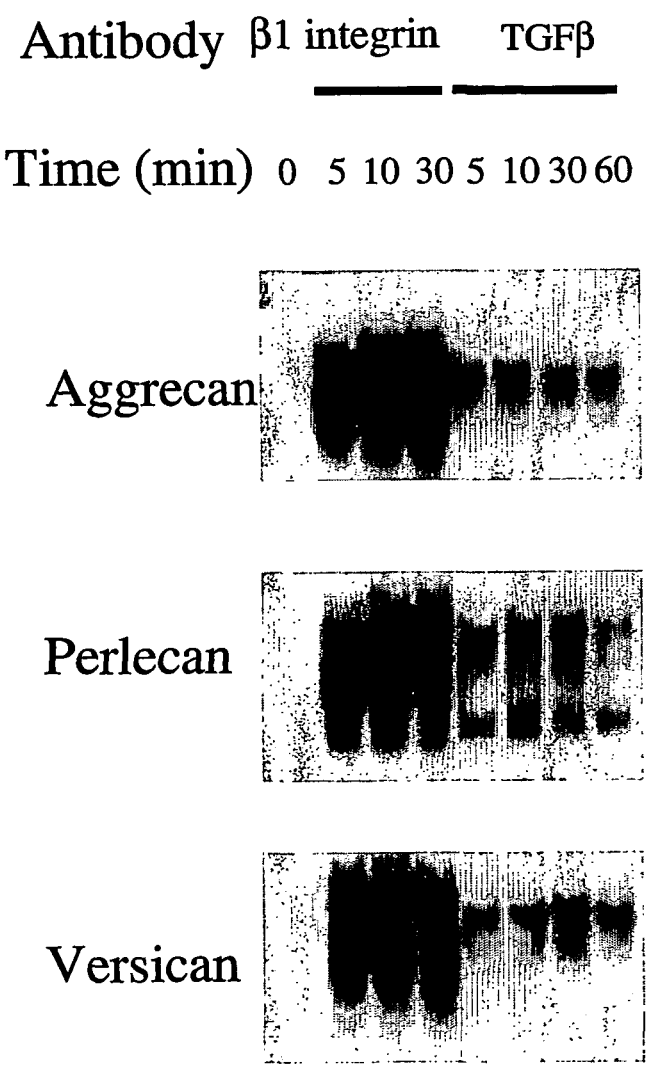

Morishima Y et al. Beta-amyloid induces neuronal apoptosis via a mechanism that involves the c-Jun N-terminal kinase pathway and the induction of Fas ligand. J Neurosci. Oct. 1, 2001;21(19):7551-60.*

Palosaari, Heidi. Matrix metalloproteinases (MMPs) and their specific tissue inhibitors (TIMPs) in mature human odontoblasts and pulp tissue: The regulation of expressions of fibrillar collagens, MMPs and TIMPs by growth factors, . . . TGF-β1) and bone morphogenetic protein-2 (BMP-2). Dissertation, University of Oulu, Oulu Finland 2003, pp. 1-108.* http://en.wikipedia.org/wiki/Regeneration_(biology), Regeneration (biolgoy), pp. 1-9, 2011.* http://en.wikipedia.org/wiki/Regenerative_medicine, Regenerative medicine, pp. 1-6, 2011.*

Kadowaki H et al. Amyloid beta induces neuronal cell death through ROS-mediated ASK1 activation. Cell Death Differ. Jan. 2005;12(1):19-24.*

Liu et al. Expression of integrin beta1 by fibroblasts is required for tissue repair in vivo. J Cell Sci. Nov. 1, 2010;123(Pt 21):3674-82.*

Werb et al. Signal transduction through the fibronectin receptor induces collagenase and stromelysin gene expression. J Cell Biol. 1989;109:877-889.*

Conant et al. Matrix metalloproteinase-1 activates a pertussis toxin-sensitive signaling pathway that stimulates the release of matrix metalloproteinase-9. Journal of Neurochemistry, 2002, 82, 885-893.*

Ohnishi et al. Matrix metalloproteinase-mediated extracellular matrix protein degradation in human pulmonary emphysema. Lab Invest. Sep. 1998;78(9):1077-87.*

Betsuyaku et al. Neutrophil Granule Proteins in Bronchoalveolar Lavage Fluid from Subjects with Subclinical Emphysema. Am J Respir Crit Care Med 1999;159:1985-1991.*

Segura-Valdez et al. Upregulation of Gelatinases A and B, Collagenases 1 and 2, and Increased Parenchymal Cell Death in COPD. Chest 2000; 117:684-694.*

Lorenzl et al. Increased plasma levels of matrix metalloproteinase-9 in patients with Alzheimer's disease. Neurochemistry International 43 (2003) 191-196.*

Itoh et al. The Role of Matrix Metalloproteinase-2 and Matrix Metalloproteinase-9 in Antibody-Induced Arthritis. The Journal of Immunology, 2002, 169: 2643-2647.*

Stahle-Backdahl et al, 92-kD Gelatinase Is Produced by Eosinophils at the Site of Blister Formation in Bullous Pemphigoid and Cleaves the Extracellular Domain of Recombinant 180-kD Bullous Pemphigoid Autoantigen. J. Clinical Invest., 93:2022-2030 (1994)).* de Fougerolles et al. Regulation of inflammation by collagen-binding integrins α1β1 and α2β1 in models of hypersensitivity and arthritis. J. Clin. Invest. 105:721-729 (2000).*

Foronjy et al. Progressive adult-onset emphysema in transgenic mice expressing human MMP-1 in the lung. Am J Physiol Lung Cell Mol Physiol. May 2003;284(5):L727-37.*

Choe et al. Methylprednisolone causes matrix metalloproteinase-dependent emphysema in adult rats. Am J Respir Crit Care Med. Jun. 1, 2003;167(11):1516-21. Epub Jan. 9, 2003.*

Wei et al. Urokinase Receptors Promote β1 Integrin Function through Interactions with Integrin α3β1. Mol. Biol. Cell Oct. 1, 2001 vol. 12 No. 10 2975-2986.*

Ahmed et al. Downregulation of urokinase plasminogen activator receptor expression inhibits Erk signalling with concomitant suppression of invasiveness due to loss of uPAR-β1 integrin complex in colon cancer cells. British Journal of Cancer (2003) 89, 374-384.*

Kondo et al. Connective tissue growth factor increased by hypoxia my initiate angiogenesis in collabroation wit matrix metalloproteinases. Carcinogenesis, 23(5):769-776, 2002.*

Churg et al, Effect of an MMP-9/MMP-12 inhibitor on smoke-induced emphysema and airway remodelling in guinea pigs. Thorax 2007, 62:706-713.*

Howeltt et al. Cellular growth and survival are mediated by β1 integrins in normal human breast epithelium but not in breast carcinoma. Journal of Cell Science 108, 1945-1957 (1995).*

NICE National Institute for Health and Care Excellence. Chronic obstructive pulmonary disease: Management of chronic obstructive pulmonary disease in adults in primary and secondary care (partial update). http://www.nice.org.uk/guidance/cg101/chapter/guidance. Jun. 2010.*

Steinmeyer et al The proteoglycan metabolism, morphology and viability of articular cartilage treated with a synthetic matrix metalloprotcinase inhibitor. Res Exp Med (1997) 197:63-79.*

Hamada et al. Suppression of adjuvant arthritis of rats by a novel matrix metalloproteinase-inhibitor. British Journal of Pharmacology (2000) 131, 1513-1520.*

Perlecan. https://en.wikipedia.org/wiki/Perlecan, Aug. 20, 2015. p. 1-19.*

Lagente et al. Role of matrix metalloproteinases in the development of airway inflammation and remodeling. Brazilian Journal of Medical and Biological Research (2005) 38: 1521-1530.*

Foronjy et al. Progressive adult-onset emphysema in transgenic mice expressing human MMP-1 in the lung. Am J Physiol Lung Cell Mol Physiol 284: L727-L737, 2003.*

Festuccia et al. Bombesin-dependent pro-MMP-9 activation in prostatic cancer cells requires betal integrin engagement. Exp Cell Res. Oct. 15, 2002;280(1):1-11.*

Buisson et al. Gelatinase B is involved in the in vitro wound repair of human respiratory epithelium. J Cell Physiol. Feb. 1996;166(2):413-26.*

Richard Grose et al., "A crucial role of β1 integrins for keratinocyte migration in vitro and during cutaneous wound repair," *Development*, 2002, vol. 129, pp. 2303-2315.

John A. Wilkins et al., "Control of $β_1$ Integrin Function: Localization of Stimulatory Epitopes", *The Journal of Biological Chemistry*, Feb. 9, 1996, vol. 271, No. 6, pp. 3046-3051.

Yaojiong Wu et al., "$β_1$-Integrin-mcdiated Glioma Cell Adhesion and Free Radical-induced Apoptosis Are Regulated by Binding to a C-terminal Domain of PG-M/Versican," *The Journal of Biological Chemistry*, Apr. 5, 2002, vol. 277, No. 14, pp. 12294-12301.

Mei Sun et al., "Temporal Response and Localization of Integrins β1 and β3 in the Heart after Myocardial Infarction: Regulation by Cytokines," *Circulation*, Feb. 25, 2003, vol. 107, No. 7, pp. 1046-1052.

Cord Brakebusch et al., "Genetic analysis of β1 integrin function: confirmed, new and revised roles for a crucial family of cell adhesion molecules," *Journal of Cell Science*, 1997, vol. 110, pp. 2895-2904.

Loubna Hassanich et al., "Generation of a Monoclonal Antibody to a Cryptic Site Common to Both Integrin β1 as Well as Gelatinase MMP9," *Hybridoma and Hybridomics*, 2003, vol. 22, No. 5, pp. 285-292.

Bongartz, T. et al., "Incidence and Mortality of Interstitial Lung Disease in Rheumatoid Arthritis: a Population-Based Study," *Arthritis & Rheumatism*, Jun. 1010, vol. 62, No. 6, pp. 1583-1591.

Chaouat, A. et al., "Pulmonary Hypertension: Basic Concepts for Practical Management," *European Respiratory Journal*, 2008, vol. 32, No. 5, pp. 1371-1385.

Crosby, L.M. et al., "Epithelial Repair Mechanisms in the Lung," *Am. J. Physiol. Lung Cell Mol. Physiol.*, Jun. 2010, vol. 298, pp. L715-L731.

Dumin, J.A. et al., "Pro-Collagenase-1 (Matrix Metalloproteinase-1) Binds the $α_2β_1$ Integrin upon Release from Keratinocytes Migrating on Type I Collagen," *The Journal of Biological Chemistry*, Aug. 3, 2001, vol. 276, No. 31, pp. 29368-29374.

Festuccia, C. et al., "Bombesin-Dependent Pro-MMP-9 Activation in Prostatic Cancer Cells Requires β1 Integrin Engagement," *Experimental Cell Research*, 2002, vol. 280, pp. 1-11.

Fischer, C. et al., "Lymphocyte-Endothelial Interactions in Inflamed Synovia: Involvement of Several Adhesion Molecules and Integrin Epitopes," *Scand. J. Immunol.*, 1993, vol. 38, No. 158, pp. 158 to 166.

Hung, W.W. et al., "Cognitive Decline among Patients with Chronic Obstructive Pulmonary Disease," *Am. J. Respir. Crit. Care Med.*, 2009, vol. 180. pp. 134-137 (2009).

Kozora, E. et al., "Cognitive Functioning in Patients with Chronic Obstructive Pulmonary Disease and Mild Hypoxemia Compared

(56) References Cited

OTHER PUBLICATIONS with Patients with Mild Alzheimer Disease and Normal Controls," *Neuropsychiatry, Neuropsychology, and Behavioral Neurology*, 1999, vol. 12, No. 3, pp. 178-183.

Levkau, B. et al., "Activation of Metalloproteinases and their Association with Integrins: an Auxiliary Apoptotic Pathway in Human Endothelial Cells," *Cell Death and Differentiation*. 2002, vol. 9, pp. 1360-1367.

Lim, S, et al., "Balance of Matrix Metalloprotease-9 and Tissue Inhibitor of Metalloprotease-1 from Alveolar Macrophages in Cigarette Smokers: Regulation by Interleukin-10," *American Journal of Respiratory and Critical Care Medicine*, 2000, vol. 162, pp. 1355-1360.

Lo Coco D. et al., "Increased Frequency of Restless Legs Syndrome in Chronic Obstructive Pulmonary Disease Patients," *Sleep Medicine*, 2009, vol. 10, pp. 572-576.

Luo, B.H. et al., "Allosteric $\beta_1$ Integrin Antibodies that Stabilize the Low Affinity State by the Preventing the Swing-Out of the Hybrid Domain," *The Journal of Biological Chemistry*, Jun. 25, 2004, vol. 279, No. 26, pp. 27466-27471.

Murphy, D.B et al., "Adverse Ventilatory Strategy Causes Pulmonary-to-Systemic Translocation of Endotoxin," *American Journal of Respiratory and Critical Care Medicine*, 2000, vol. 162, pp. 27-33.

Ortapamuk, H. et al., "Brain Perfusion Abnormalities in Chronic Obstructive Pulmonary Disease: Comparison with Cognitive Impairment," *Annals of Nuclear Medicine*, 2006, vol. 20, No. 2, pp. 99-106.

Saito, Y. et al., "Potentiation of Cell Invasion and Matrix Metalloproteinase Production by $\alpha3\beta1$ Integrin-Mediated Adhesion of Gastric Carcinoma Cells to Laminin-5", *Clin. Exp. Metastasis*, 2010, vol. 27, pp. 197-205.

Shapiro, S.D. et al., "Activation of the 92-kDa Gelatinase by Stromelysin and 4-Aminophenylmercuric Acetate," *The Journal of Biological Chemsitry*, Mar. 17, 1995, vol. 270, No. 11, pp. 6351-6356.

Tremblay, L. et al., "injurious Ventilatory Strategies Increase Cytokines and *c-fos* m-RNA Expression in an Isolated Rat Lung Model," *J. Clin. Invest.*, Mar. 1997, vol. 99, No. 5, pp. 944-952.

Tsuji, T. et al., "Regulation of Melanoma Cell Migration and Invasion by Laminin-5 and $\alpha3\beta1$ Integrin (VLA-3)," *Clinical & Experimental Metastasis*, 2002, vol. 19 pp. 127-134.

Wang, J. et al., "Neuroprotection by Inhibition of Matrix Metalloproteinases in a Mouse Model of Intracerebral Haemorrhage," *Brain*, 2006, vol. 128, pp. 1622-1633.

Zhao, B-Q. et al., Role of Matrix Metalloproteinases in Delayed Cortical Responses after Stroke: *Nature Medicine*, Apr. 2006, vol. 12, No. 4, pp. 441-445.

Arroyo, A. G. et al., "Regulation of the VLA Integrin-Ligand Interactions through the $\beta1$ Subunit,", *J. Cell Biol.*, May 1992, vol. 117, No. 3, pp. 659-670.

Kamiguti, A. S. et al., "Inhibition of collagen-induced platelet aggregation as the result of cleavage of $\alpha_2\beta_1$-integrin by the snake venom metalloproteinase jararhagin," *Biochem. J.*, Dec. 1996, vol. 320, No. 2, pp. 635-641.

Rahilly, M.A. et al., "The Specificity of Integrin-Ligand Interactions in Cultured Human Renal Epithelium," *J Pathol.*, Jul. 1993, vol. 170, No. 3, pp. 297-303.

Ni, H. et al., "Localisation of a Novel Adhesion Blocking Epitope on the Human $\beta1$ Integrin Chain," *Cell Adhes. Commun.*, Jun. 1998, vol. 5. No. 4, pp. 257-271.

Zhang, Z. et al., "The $\alpha5\beta1$ integrin supports survival of cells on fibronectin and up-regulates Bcl-2 expression," *Proc. Natl. Acad. Sci. USA*, Jun. 1995, vol. 92, No. 13, pp. 6161-6165.

Di Persio, C.M. et al., "Mouse keratinocytes immortalized with large T antigen acquire $\alpha3\beta1$ integrin-dependent secretion of MMP-9/gelatinase B," *J. Cell Sci.*, Aug. 2000, vol. 113, No. 16, pp. 2909-2921.

Albuquerque, M.L.C. et al., "Lamellipodial Motility in Wounded Endothelial Cells Exposed to Physiologic Flow Is Associated With Different Patterns of $\beta_1$-Integrin and Vinculin Localization," *J Cell. Physiol.*, Apr. 2003, vol. 195, No. 1, pp. 50-60.

\* cited by examiner

Figure 1. The effect of β1 integrin functional modification on proteoglycans in H441 cells Figure 3. The effect of modulation of β1 integrin on perlecan expression in human lung explants.
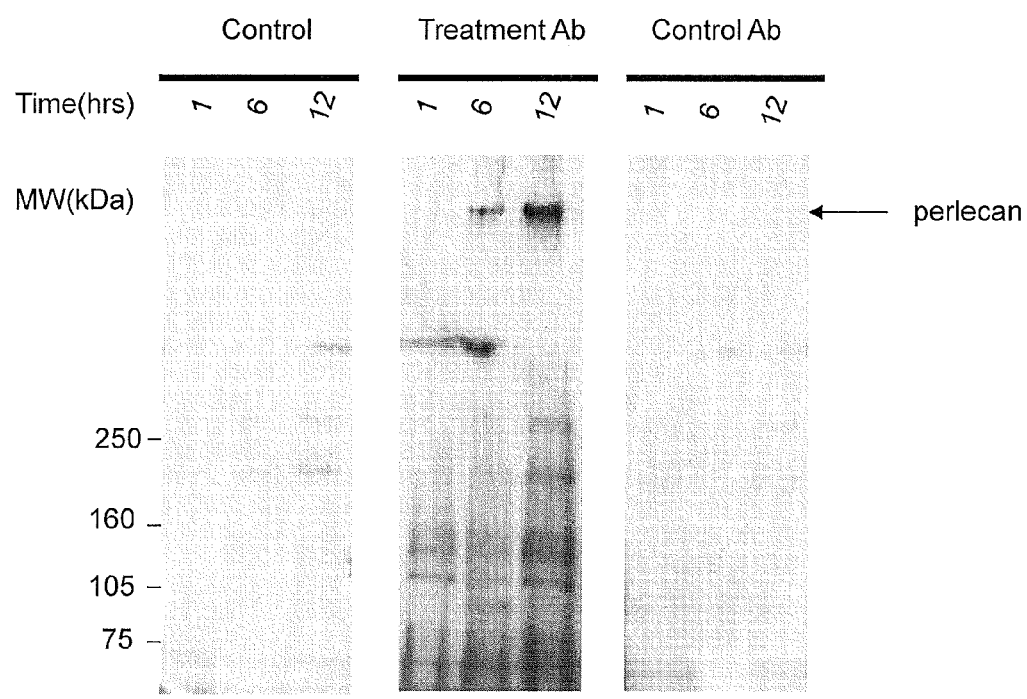

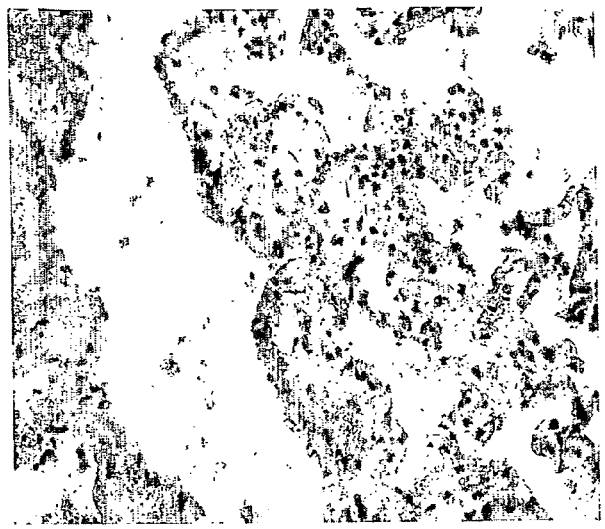
Figure 4. The effect of β1 functional modification on perlecan expression in human lung explants.

Figure 5. The effect of β1 integrin functional modification on MMP9 in human lung explants
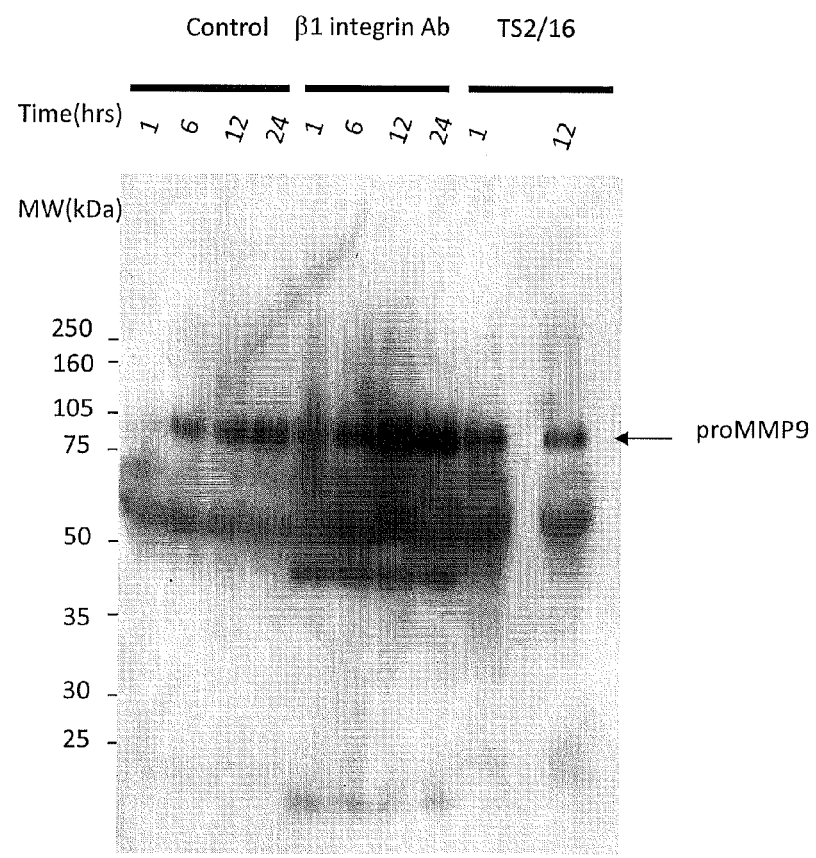

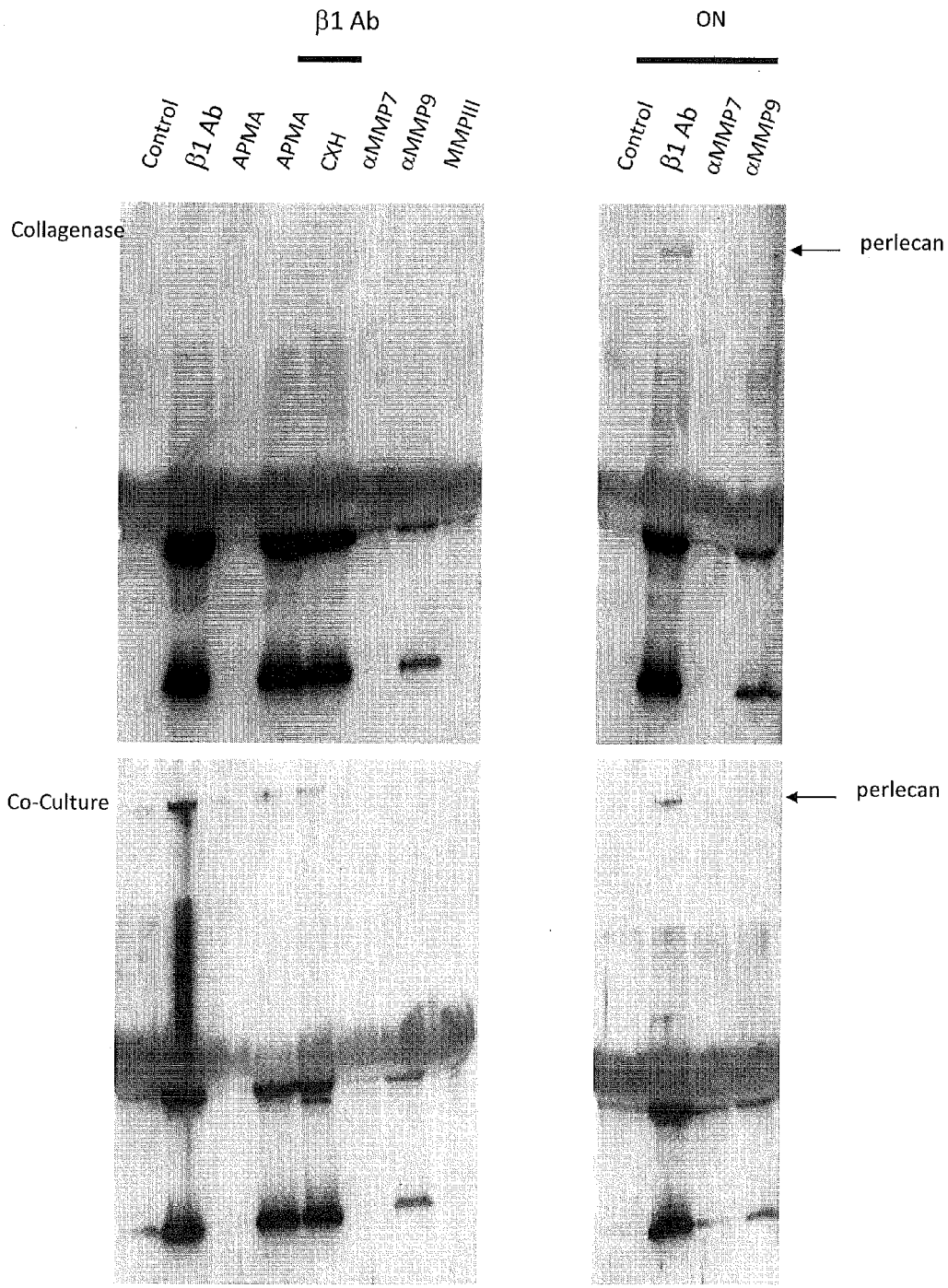
Figure 6. The effect of β1 integrin functional modification on perlecan in cultured human lung cells

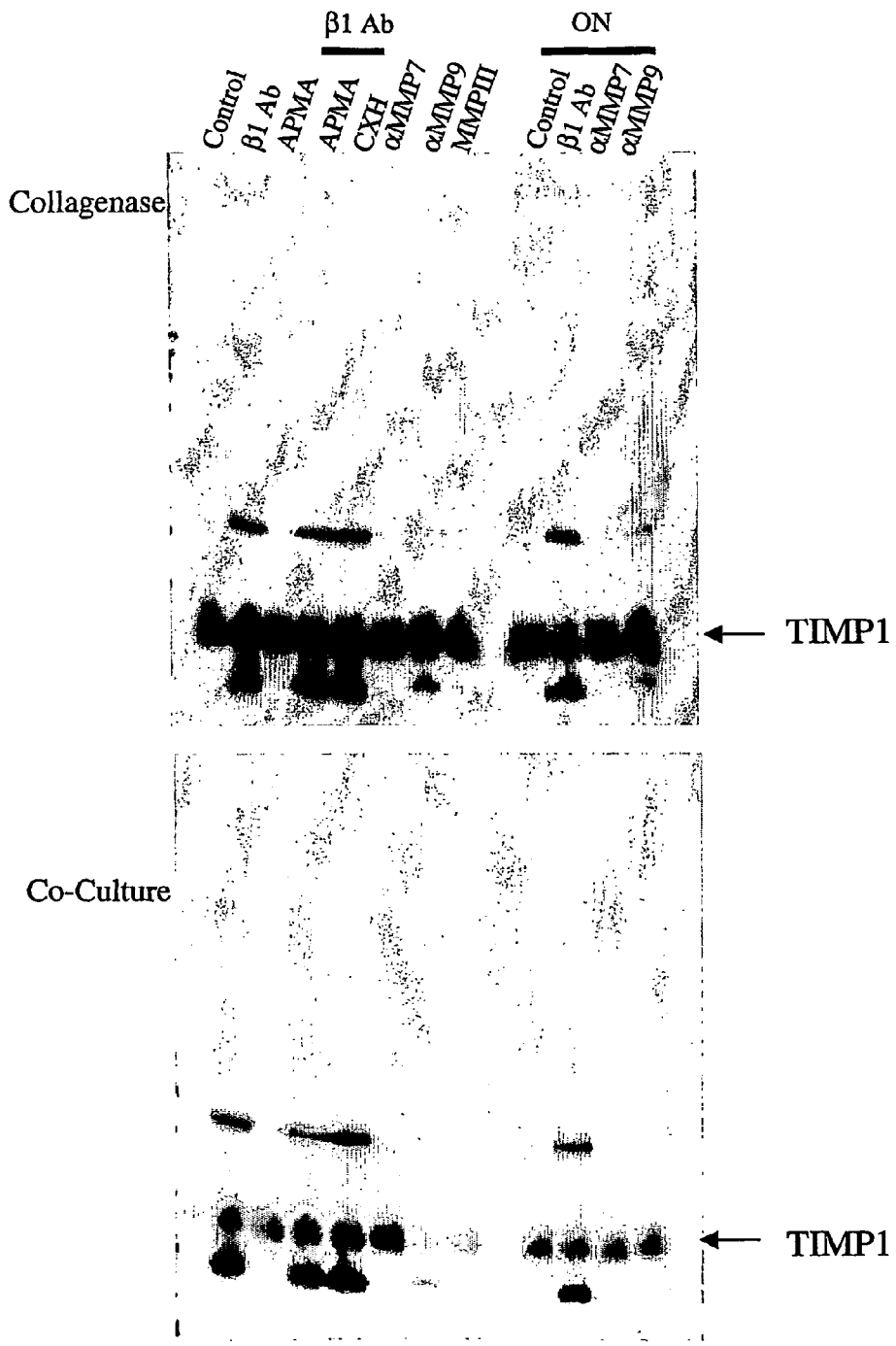
Figure 7. The effect of β1 integrin functional modification on TIMP1 in cultured human lung cells

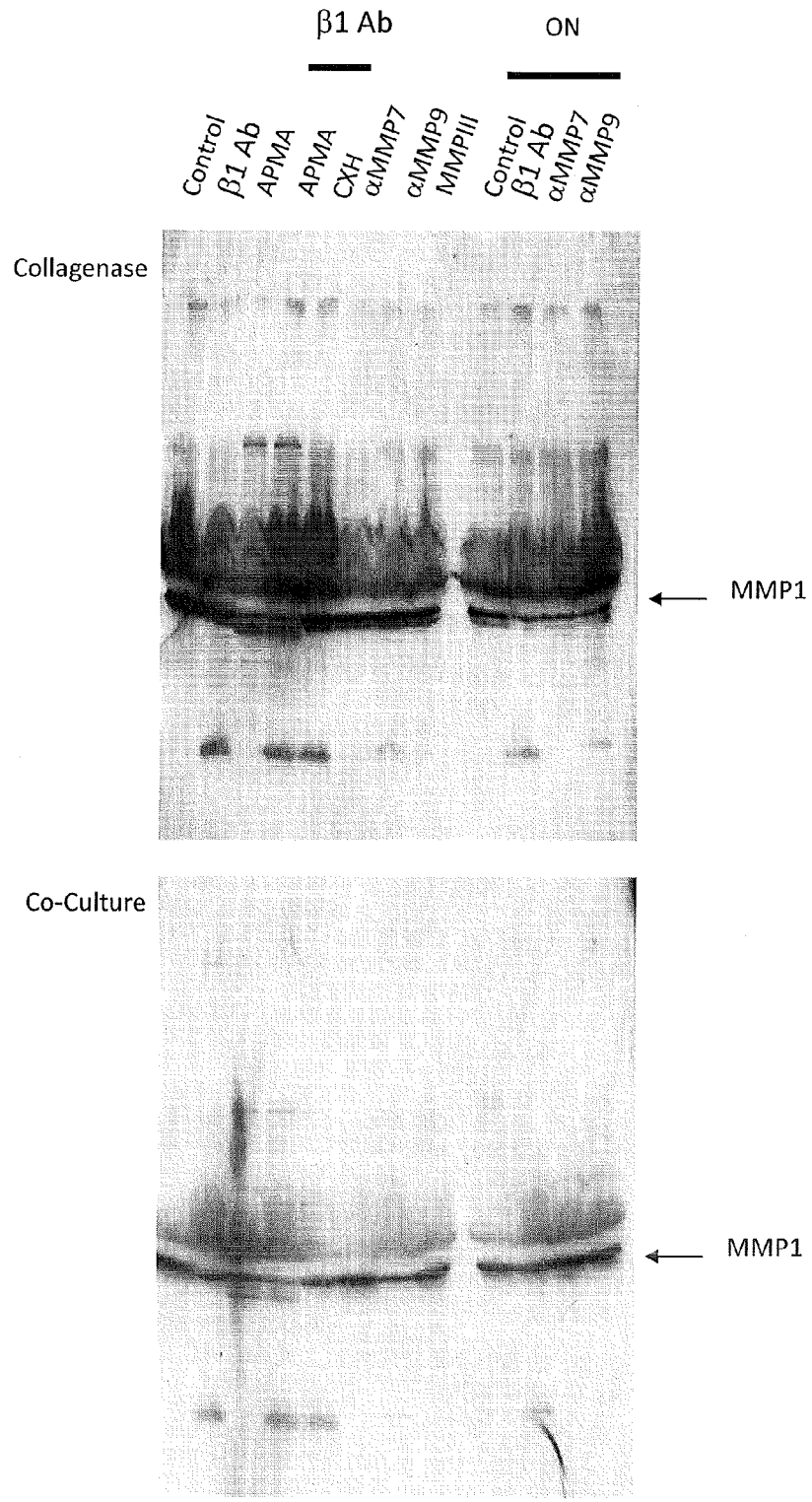
Figure 8. The effect of β1 integrin functional modification on MMP1 in cultured human lung cells Figure 9. The effect of β1 integrin functional modification on MMP9 in cultured human lung cells
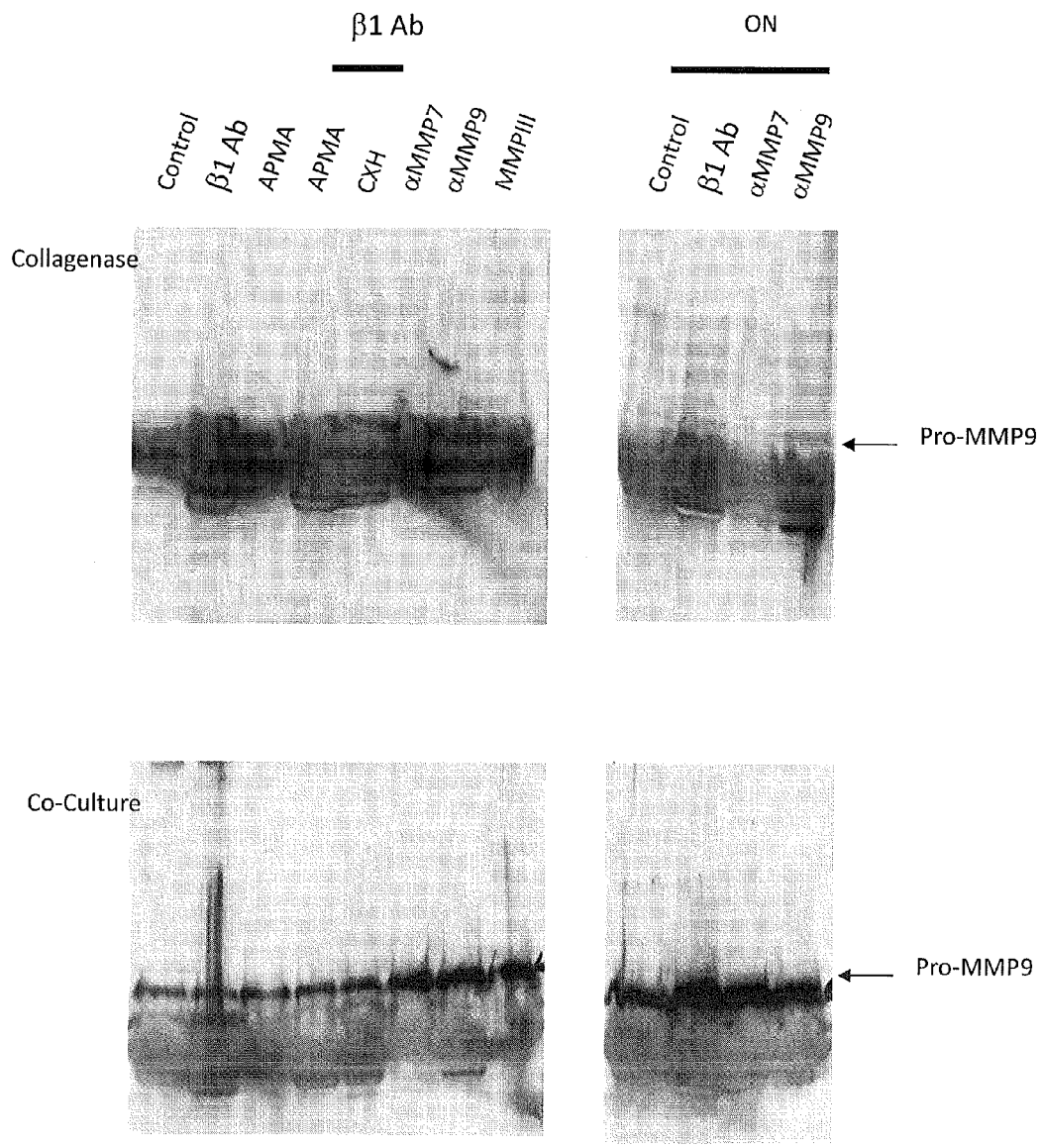

Figure 12:
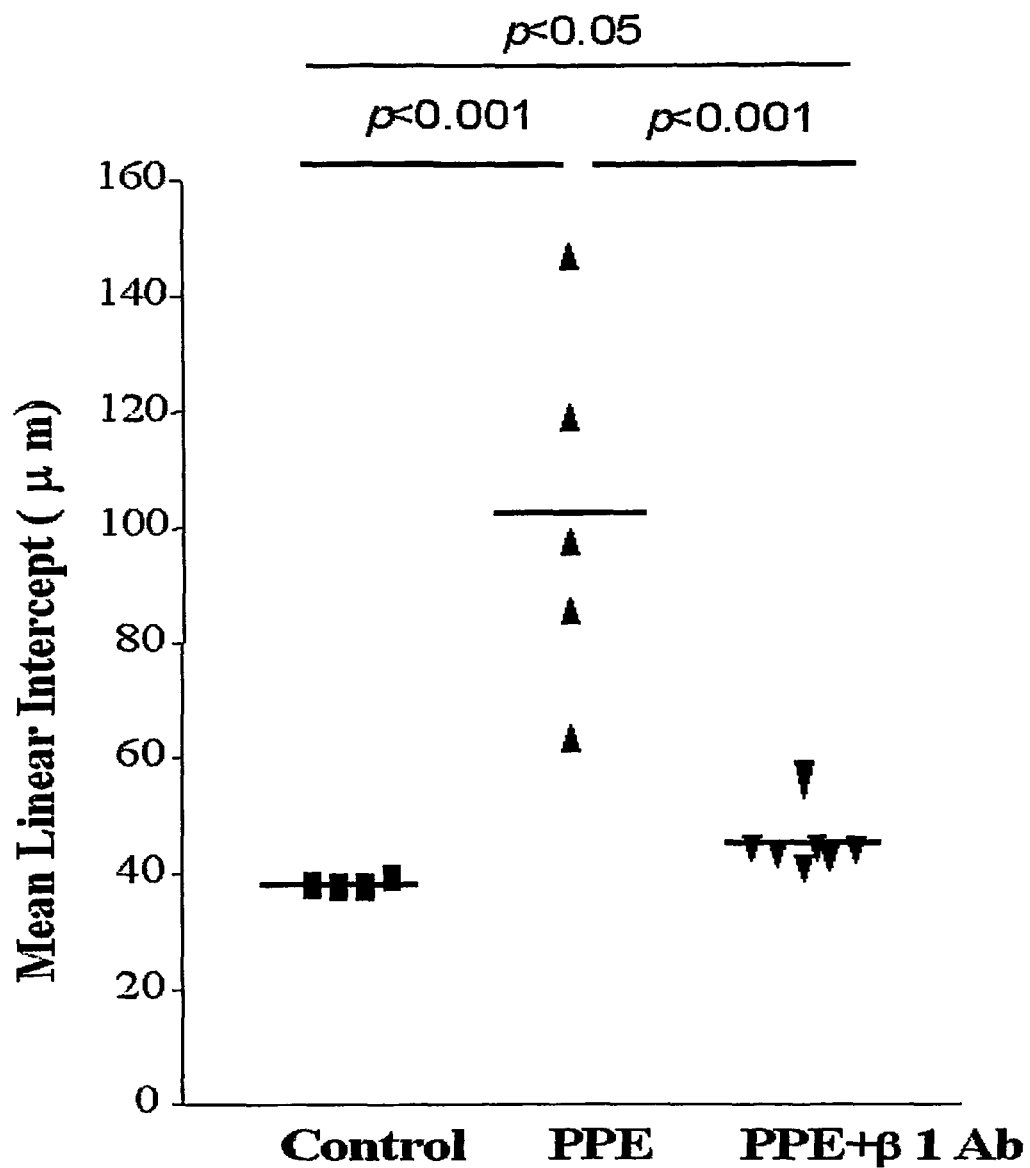
Figure 13:
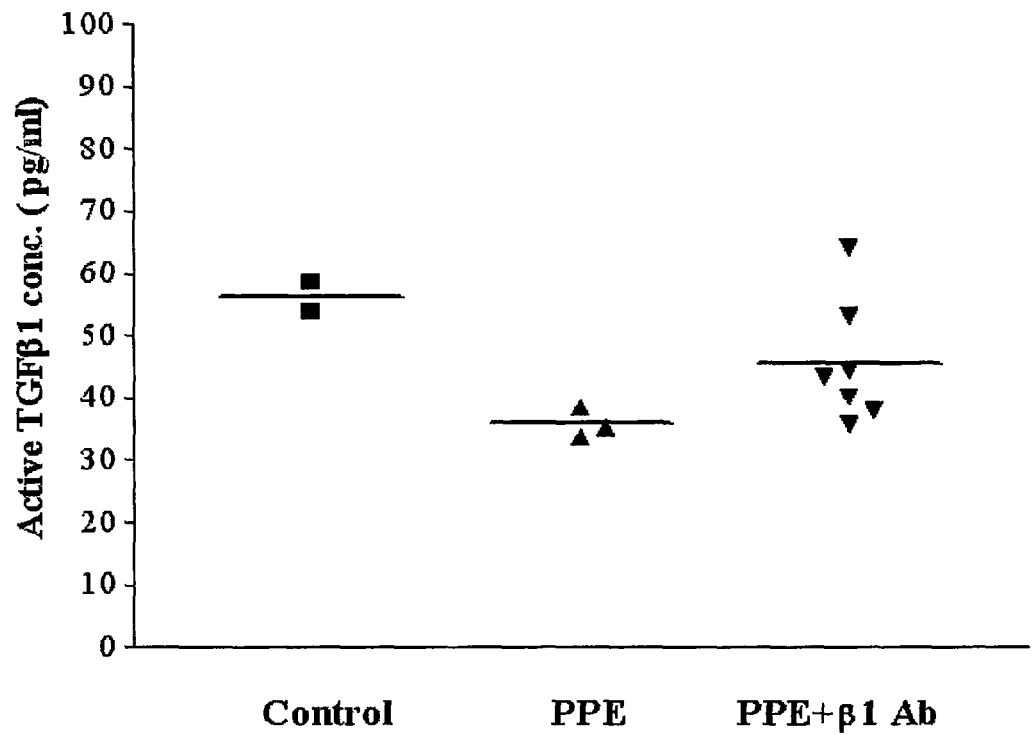
Figure 14:
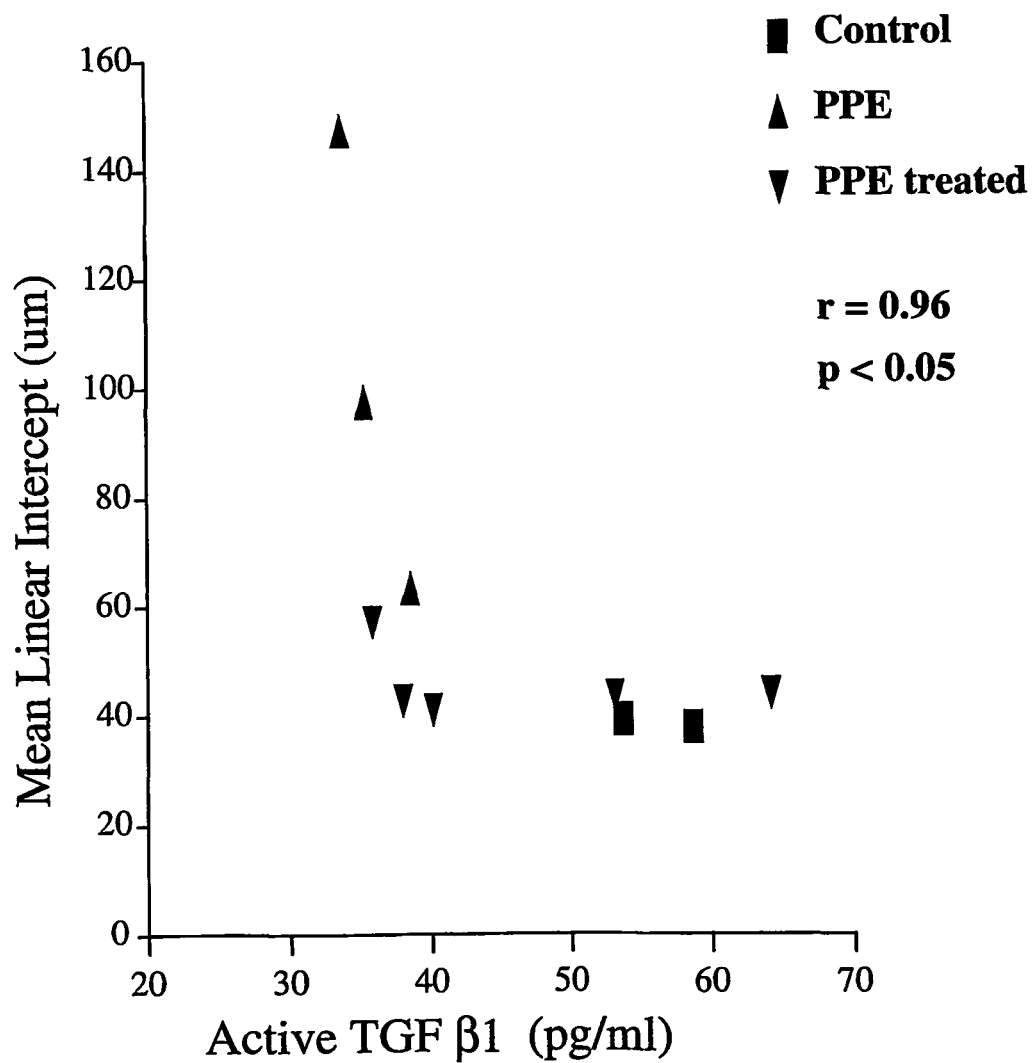

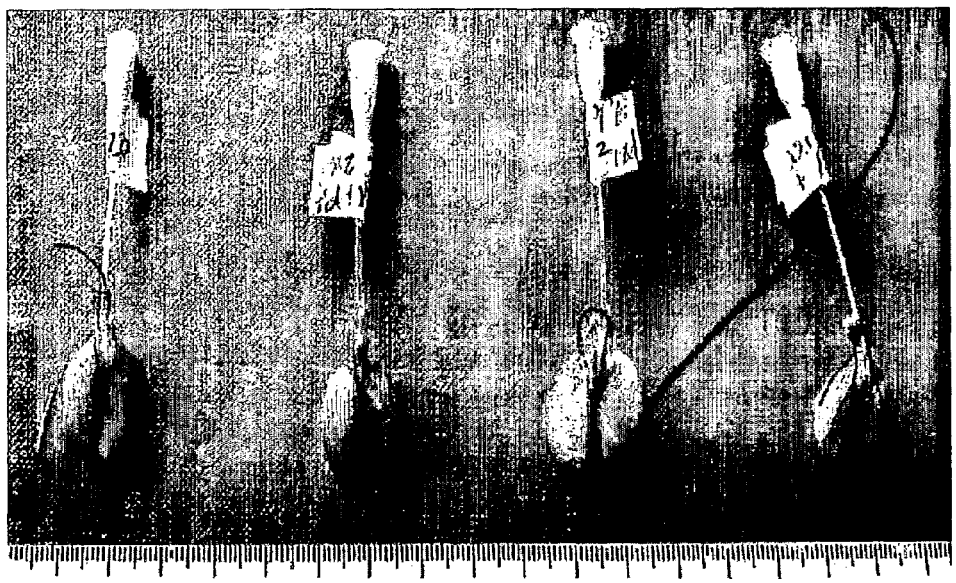
Control    3.5 U PPE    19.5 U PPE    19.5 U PPE
+ anti β1 integrin
Figure 10. The effect of b1 integrin modulation on emphysematous lungs Figure 12. The effect of beta 1 integrin antibody on a space enlargement in elastase-induced emphysema in mice Figure 13. The effect of β1 integrin antibody on TGFβ1 levels in BAL fluid in elastase-induced emphysema in mice Figure 14. The relationship between airspace enlargement and TGF beta 1 levels in BAL fluid in mice Figure 15. The effect of β1 integrin functional modification on perlecan in NCI-H441 human lung epithelial cell line Figure 16. The effect of β1 integrin functional modification on inactive MMP9 in NCI-H441 human lung epithelial cell line

| | | K | Raw | G | H | Lm | Quasi-static Elastance | PeakPressure |
|---|---|---|---|---|---|---|---|---|
| K | Pearson Correlation | 1.000 | 0.156 | -0.358 | -0.693 | 0.605 | -0.648 | -0.743 |
| | Sig. (2-tailed) | | 0.269 | 0.009 | 0.000 | 0.000 | 0.000 | 0.000 |
| | N | 52 | 52 | 52 | 52 | 49 | 51 | 51 |
| Raw | Pearson Correlation | 0.156 | 1.000 | -0.023 | -0.007 | -0.063 | -0.184 | 0.037 |
| | Sig. (2-tailed) | 0.269 | | 0.874 | 0.963 | 0.666 | 0.195 | 0.798 |
| | N | 52 | 52 | 52 | 52 | 49 | 51 | 51 |
| G | Pearson Correlation | -0.358 | -0.023 | 1.000 | 0.721 | -0.556 | 0.429 | 0.072 |
| | Sig. (2-tailed) | 0.009 | 0.874 | | 0.000 | 0.000 | 0.002 | 0.618 |
| | N | 52 | 52 | 52 | 52 | 49 | 51 | 51 |
| H | Pearson Correlation | -0.693 | -0.007 | 0.721 | 1.000 | -0.544 | 0.455 | 0.405 |
| | Sig. (2-tailed) | 0.000 | 0.963 | 0.000 | | 0.000 | 0.001 | 0.003 |
| | N | 52 | 52 | 52 | 52 | 49 | 51 | 51 |
| Lm | Pearson Correlation | 0.605 | -0.063 | -0.556 | -0.544 | 1.000 | -0.573 | -0.600 |
| | Sig. (2-tailed) | 0.000 | 0.666 | 0.000 | 0.000 | | 0.000 | 0.000 |
| | N | 49 | 49 | 49 | 49 | 50 | 48 | 48 |
| Quasi-static Elastance | Pearson Correlation | -0.648 | -0.184 | 0.429 | 0.455 | -0.573 | 1.000 | 0.591 |
| | Sig. (2-tailed) | 0.000 | 0.195 | 0.002 | 0.001 | 0.000 | | 0.000 |
| | N | 51 | 51 | 51 | 51 | 48 | 51 | 51 |
| Peak Pressures | Pearson Correlation | -0.743 | 0.037 | 0.072 | 0.405 | -0.600 | 0.591 | 1.000 |
| | Sig. (2-tailed) | 0.000 | 0.798 | 0.618 | 0.003 | 0.000 | 0.000 | |
| | N | 51 | 51 | 51 | 51 | 48 | 51 | 51 |

[**] Correlation is significant at the 0.01 level (2-tailed).
[*] Correlation is significant at the 0.05 level (2-tailed).

Figure 30 – Table 1

TISSUE REPAIR BY MODULATION OF BETA-1 INTEGRIN BIOLOGICAL FUNCTION

FIELD OF THE INVENTION

The present invention relates to methods of and compounds for repairing tissue where the extracellular matrix is degraded. More particularly, the invention relates to compounds including antibodies which increase extracellular matrix anabolism and the identification of a novel pathway to identify compounds which are capable of being used in therapy to increase extracellular matrix anabolism.

SEQUENCE LISTING

The instant application contains a Sequence Listing which has been submitted via EFS-Web and is hereby incorporated by reference in its entirety.

BACKGROUND TO THE INVENTION

The Extracellular Matrix: Composition and Structure

The extracellular matrix (ECM) is a complex composite of proteins, glycoproteins and proteoglycans (PGs). Awareness of this complexity has been heightened by the recognition that ECM components, individually or in concert with each other or other extracellular molecules, profoundly influence the biology of the cell and hence of the physiology of the whole structure in to which the cell is embedded. The functions of the ECM described so far are many but can be simply categorised as control of cell growth, providing structural support and physical stabilization, affecting cell differentiation, orchestrating development and tuning metabolic responses (42).

PGs are a family of heterogeneous and genetically unrelated molecules. The number of full-time as well as part-time members is constantly expanding. The terms 'full-time' and 'part-time' refer to the fact that some known PGs can exist as glycoproteins and some proteins can be found in a glycosylated form. In general, PGs are composed of a core protein to which one or more Glycosaminoglycan (GAG) chains are covalently attached by N or O linkage. GAGs are highly anionic linear heteropolysaccharides made of a disaccharide repeat sequences (53). However, there have been reports of PGs devoid of the GAG side chain (4; 106). GAGs can be classified into four distinct categories based on their chemical composition (53). The first category is the chondroitin/dermatan sulphate (CS/DS) chain consisting of alternating galactosamine and glucuronic/iduronic acid units. A second class, which is by far the most structurally diverse, is the heparin/heparan sulphate (H/HS) group which is composed of alternating glucosamine and glucuronic/iduronic repeats. The third type is the glucosamine and galactose containing keratan sulphate (KS) GAG. Hyaluronic acid (HA) is composed of glucosamine and glucuronic acid repeats. It is the most distinct GAG since it is not sulphated and is not covalently linked to the core protein of PG. Instead, HA binding to the PG core protein is mediated by a class of proteins known as HA binding proteins which exist in the ECM, on the cell surface and intracellularly (93).

Perlecan is a large HSPG with a core protein size of 400-450 kDa known to possess three HS chains. It was first isolated by Hassell et al. (44). It acquired its name from its appearance in rotary shadowing electron microscopy where it looks like a pearl on a string. It is a large multi-domain protein and thus one of the most complex gene products (23; 52).

Domain I is the N-terminus, this containing acidic amino acid residues which facilitate the polymerisation of heparan sulphate (52). However, recombinant domain I has been shown to accept either HS or CS chains; an observation that has been confirmed by in-vitro studies characterizing PGs synthesized in response to transforming growth factor β (TGF-β) and foetal calf serum showing that perlecan can be synthesized with CS chains (13). Ettner et al. (26) have shown that the ECM glycoprotein laminin, binds to perlecan domain I, as well as domain V both of which can carry the HS side chain. Loss of the HS chain abolished the binding.

Globular domain II was postulated to mediate ligand binding by the low-density lipoprotein (LDL) receptor due to their homology (30; 79). Heparitinase treatment abrogates this interaction pointing to the fact that the HS GAG side chains are involved in the binding (30).

Domain III of perlecan contains an RGD tripeptide sequence that provides a binding capacity for integrin receptors and provides anchorage for the 19, cell (18). Yamagata et al. have shown using double-immunofluorescence that perlecan colocalizes with integrins in cultured fibroblasts (104). This domain has also been shown to be homologous to the laminin short arm (51).

Domain IV is the largest domain of perlecan containing a series of immunoglobulin (Ig)-like repeats similar to those found in the Ig superfamily of adhesion molecules leading to the speculation that it may function in intermolecular interactions (47). Finally, domain V possessing three globular domains homologous to the long arm of laminin is thought to be responsible for self-assembly and laminin mediated cell adhesion (14).

The multiplicity and variety of perlecan's structural domains are indicative of its potential functions. Perlecan, in addition to binding to laminin and integrins, has been shown to bind fibronectin via its core protein (51). The HS chains of perlecan also have a very important functional role which has proven to be diverse. It has been reported that perlecan mediates the interaction between skeletal muscle cells and collagen IV via the HS GAG side chain (98). Recent studies have led to the identification and characterization of perlecan as a ligand for L-selectin in the kidney (65). Whether this interaction is via the core protein and/or the HS side chain is not clear. The group of Varki has identified in a series of experiments the HS GAG as well as heparin from endothelial cells as a ligand for both L- and P-selectins but not E-selectins (59; 80). The HS side chains in general, and those attached to perlecan core protein in particular, are known to bind growth factors such as fibroblast growth factors (FGF)-2, FGF-7, TGF-β, platelet factor-4 and platelet-derived growth factor-BB (PDGF-BB) (31; 52). The functional significance of these interactions has been highlighted by numerous studies demonstrating the role of perlecan in angiogenesis (5; 87), the control of smooth muscle cell growth (10) and the maturation and maintenance of basement membranes (19). The functional importance of perlecan has been demonstrated by a study of mice lacking perlecan gene expression (19). Homozygous null mice died between embryonic days 10 and 12. The basement membranes normally subjected to increased mechanical stresses such as the myocardium lost their integrity and as a result small clefts formed in the cardiac muscle leading to bleeding in the pericardial sac and cardiac arrest. The homozygotes also had severe cartilage defects characterised by chondrodysplasia despite that fact that it is a tissue which normally lacks basement membrane. This finding was interpreted as a potential proteolysis-protective function for perlecan in cartilage (19). The delay in detecting abnormalities until E10 suggests a certain redundancy with compensatory molecules being able to substitute for perlecan such as the basement membrane HSPGs collagen XVIII (38) and agrin (36).

Large aggregating PGs are, to date, composed of four members; versican, aggrecan, neurocan and brevican (52). The hallmark of these PGs is the ability to bind hyaluronic acid forming highly hydrated aggregates. They are also characterized by their tridomain structure composed of an N-terminal domain where HA binding occurs, a central domain carrying the GAG side chains and lectin binding C-terminus.

Versican is a PG with a core protein of 265-370 kDa which was originally isolated from human fibroblasts and is the homolog of the avian PG-M (110). It can possess 10-30 chains of CS and has been also reported to carry KS GAG chains (109). It is expressed by keratinocytes, smooth muscle cells of the vessels, brain and mesengial cells of the kidney. The N-terminal domain is responsible for the hyaluronic acid binding properties of versican (61). The central domain of versican consists of the GAG binding subdomains, GAG-$\alpha$ and GAG-$\beta$. These subdomains are encoded by two alternatively spliced exons and this gives rise to different versican isoforms. To date four isoforms have been recognized. V0 contains both GAG-$\alpha$ and GAG-$\beta$. V1 and V2 are known to possess domain GAG-$\beta$ and GAG-$\alpha$ respectively (109). V3 is the variant which contains neither of the two subdomains and hence carries no CS/DS GAG side chains and has been localized in various mammalian tissues (63; 82; 105). The third domain of versican is the C-terminus and consists of a lectin-binding domain, an EGF-like domain and a complement regulatory protein-like domain. This C-terminus binds the ECM glycoprotein, tenascin (3), heparin and heparan sulphate (88) and fibulin (2). Versican is known to have an inhibitory effect on mesenchymal chondrogenesis (108), promotes proliferation (107) and migration via the formation of pericellular matrices via its interaction with cell surface bound hyaluronic acid (27). The formation of pericellular matrices is not only achieved via the core protein association with HA but also through GAG side chain interaction with the cytoskeletal associated cell surface receptor, CD44 (55). The postulated role of versican in migration has been also further reinforced by the recent findings of its interaction with both L- and P-selectins via the CS/DS side GAG chains (56). Furthermore, versican GAG side chains modulate chemokine response (45) and has been recently reported to possess growth factor binding capacity (111) and binding to $\beta_1$ integrin Wu, Chen, et al. 2002 394.

Aggrecan is another large aggregating proteoglycan. It is known to be a major structural component of cartilage. It is composed of three globular domains and two GAG attachment domains (100). The N-terminal globular domain (G1) binds HA and link protein to form large aggregates. The second globular (G2) domain is unique to aggrecan and has no HA binding capacity. The function of this domain has not been clearly defined. The interglobular domain between the G1 and G2 contains proteolytic cleavage sites for metalloproteinases and thus been heavily investigated in pathologies where degradation of this domain is a hallmark, such as osteoarthritis. A KS domain is located at the C-terminus of the G2 domain followed by the CS domain. The CS domain is the largest domain of aggrecan and the domain which contributes to the hydrated gel-like forming capacity of aggrecan and thus its importance in load-bearing function. The last domain is the globular domain (G3) which contains three modules: an epidermal growth factor-like domain, a lectin module and a complement regulatory module. This domain is responsible for the interaction of aggrecan with the ECM glycoprotein, tenascin.

Functions of Extracellular Matrix Proteoglycans

In addition to contributing to the mechanical properties of connective tissues, extracellur matrix (ECM) PGs have biological functions which are achieved via specific classes of surface receptors. The two main classes are the syndecan and integrin receptor families (42). However, other receptors have also been described to bind ECM components such as the selecting family of glycoproteins (80), CD44 with all its variants (33), cell surface enzymes such as hyaluronic acid synthases (89), and PGs (52). The effects of the ECM do not and cannot, in an in vivo milieu, ever occur without the influence of other molecules. This statement is based on two well-described concepts. The first being that part of the effects of growth factors, cytokines, hormones and vitamins, as well as cell-to-cell contact and physical forces is alteration of the ECM production. The second concept is that the effects of the ECM on the cell bear a striking similarity to those effects observed in response to the above mentioned factors. This is a phenomenon known as "mutual reciprocity" (42) which is an oversimplified view of a complex set of modular interactions, i.e. as defined by Hartwell et al. (43) "cellular functions carried out by "modules" made up of many species of interacting molecules". The outcome is a summation of all these modules which often interact with each other in a non-vectorial manner.

Integrins are a family of $\alpha,\beta$ heterodimeric receptors that mediate dynamic linkages between extracellular adhesion molecules and the intracellular actin cytoskeleton. Although integrins are expressed by all multicellular animals, their diversity varies widely among species (49; 73; 94). To date 19 $\alpha$ and 8 $\beta$ subunit genes encode polypeptides that combine to form 25 different receptors. Integrins have been the subject of extensive research investigating the molecular and cellular basis of integrin function.

Integrins are major contributors to both the maintenance of tissue integrity and the promotion of cellular migration. Integrin-ligand interactions provide physical support for cell cohesion, generation of traction forces in cellular movement, and organise signalling complexes to modulate cellular functions such as differentiation and cell fate. PGs are key ECM components which interact with integrins modifying their function and integrins, in turn, are key regulators of ECM PGs.

Currently little is known about the mechanisms underlying tissue organisation and cellular trafficking, and the regulation of those processes in disease, as well as determining the molecular basis of integrin function. No information has been provided to identify the function of distinct regions within the receptor.

Although numerous reports have employed functional modification approaches using antibodies to $\beta1$ integrin, the functional modification by definitions remains obscure since it is mainly focused on activation or blocking of adhesion to a substrate under a defined set of conditions. The limitations of such definition are clear. Firstly, it does not take into account that unlike other receptors, integrins can exist in an inactive, active and active and occupied state. Secondly, the functional modulation is often achieved via different domains and hence may entail different downstream intracellular signalling and therefore even if the effect on adhesion is similar the functional end outcome can be different since each region appears to possess a different function (21; 48; 49; 72). Thirdly, $\beta1$ integrin exists in four different splice variants and the difference is in the cytoplasmic domain hence implicating different downstream signalling. The difference in signalling downstream effects between the splice variants is not yet defined. Therefore, the use of functional modification terminology serves best to take the above mentioned points into account since the "blocking" and "activation" of adhesion terminology refers to only one function, of many, of integrin.

Heterodimers of β1 integrin bind collgens (α1,α2), laminins (α1,α2,α3,α7,α9) and fibronectin (α3,α4,α5,α8,αv). It can also act as a cell counter receptor for molecules such as vascular cell adhesion molecule-1 (VCAM-1). Further more, recent reports have demonstrated that b1 integrin can also bind metalloproteinases such as MMP2 (64) and MMP9 (28) and affect their activation state. Both MMPs have been shown to contribute to caspase-mediated brain endothelial cell death after hypoxia-reoxygenation by disrupting cell-matrix interactions and homeostatic integrin signalling (7). TGFβ1 have also been reported to bind to β1 integrin.

The outside-in signaling of integrins is critical to its numerous cellular functions such as adhesion, proliferation, survival, differentiation, and migration. The number and type of integrin receptors heterdimer together with the availability of specific ECM substrates are important in determining which cellular functions are affected. The synthesis and insertion of new integrins into the membrane, removal from the cell surface, or both are possible mechanisms for controlling the number of available integrin receptors. It is possible that new synthesis would require upregulation of expression and sorting of specific a chains to pair with excess β1 in the cytoplasm and presentation of the new α/β heterodimer in a precise location on the cell surface, which is not a very targeted mechanism. An alternative method of regulation could be cleavage at the cell surface, or shedding, as an immediate method for removal of specific integrin-ECM contacts as it would provide a more focused mechanism for regulating specific functions. Furthermore, the shed β1 fragment could bind to cells or ECM components or alternatively be involved in signalling and biological events involved in cellular growth and remodelling. Indeed it has been shown that in myocytes and fibroblasts a change size and shape results in altered cellular contacts with the ECM. This lead to shedding of a β1 integrin fragment from the cell surface (32).

As to the role of β1 integrin in tissue injury and repair, it has been shown to be significantly activated in the infarcted myocardium. Integrin is active particularly at sites of inflammation and fibrosis (90). Integrins- and cytoskeletal-associated cytoplasmic focal adhesion proteins have been suggested to participate in the process of endothelial wound closure where treatment of human coronary artery endothelial cells with anti-β1 integrin function-modifying antibody enhanced wound closure (1). Further in vivo evidence have shown that the loss of β1 integrins in keratinocytes caused a severe defect in wound healing. β1-null keratinocytes showed impaired migration and were more densely packed in the hyperproliferative epithelium resulting in failure in re-epithelialisation. As a consequence, a prolonged inflammatory response, leading to dramatic alterations in the expression of important wound-regulated genes was seen. Ultimately, β1-deficient epidermis did cover the wound bed, but the epithelial architecture was abnormal. These findings demonstrate a crucial role of β1 integrins in wound healing (37).

Apoptosis is a form of cell death that eliminates compromised or superfluous cells. It is controlled by multiple signaling and effector pathways that mediate active responses to external growth, survival, or death factors. Cell cycle checkpoint controls are linked to apoptotic enzyme cascades, and the integrity of these and other links can be genetically compromised in many diseases, such as cancer. The defining characteristic of apoptosis is a complete change in cellular morphology where the cell undergoes shrinkage, chromatin margination, membrane blebbing, nuclear condensation and then segmentation, and division into apoptotic bodies which may be phagocytosed. DNA fragmentation in apoptotic cells is followed by cell death and removal from the tissue, usually within several hours. It is worth noting that a rate of tissue regression as rapid as 25% per day can result from apparent apoptosis in only 2-3% of the cells at any one time.

β1 integrin has also been implicated in apopotosis (76; 77; 101). Involvement of β1 integrin in beta Amyloid Protein (β-AP)-induced apoptosis in human neuroblastoma cells (12). In the presence of either collagen I degrees, fibronectin, or laminin, β-AP toxicity was severely reduced. This protective effect seems to be mediated by integrins, because preincubation of neuroblastoma cells with antibodies directed against β1 and α1 integrin subunits greatly enhanced β-AP-induced apoptosis.

Loss of activity of the β1-integrin receptor in hepatocytes, which controls adhesion to collagen, was seen to precede this loss of adhesive ability. Addition of the β1-integrin antibody (TS2/16) to cells cultured with liver injury serum significantly increased their adhesion to collagen, and prevented significant apoptosis (78). However, this effect seems controversial as experiments with an antibody to integrin β1 suggest that the collagen-chondrocyte interactions are mediated through integrin β1, and these interactions may protect chondrocytes from apoptosis (16).

It has been postulated that prior to the commitment to apoptosis, signals initiated by the apoptotic stimulus may alter cell shape together with the activation states and/or the availability of integrins, which promote matrix-degrading activity around dying cells. This pathway may interrupt ECM-mediated survival signaling, and thus accelerate the the cell death program (64).

Maintenance of the Extracellular Matrix

ECM homeostasis is maintained under normal physiological conditions by a fine balance between degradation and synthesis orchestrated by matrix metalloproteinase (MMPs) and tissue inhibitors of metalloproteinase (TIMPs). This homeostasis is critical in many physiological processes such as embryonic development, bone growth, nerve outgrowth, ovulation, uterine involution, and wound healing. MMPs also have a prominent role in pathological processes such as arthritis (66; 70; 84), chronic obstructive pulmonary disease (17; 92) and atherosclerosis (67). However, little is known about how they are anchored outside the cell.

Mechanical forces are known to modulate a variety of cell functions such as protein synthesis, proliferation, migration or survival and by doing so regulate tissue structure and function. The routes by which mechanical forces influence cell activities have been defined as mechanotransduction and include the tensegrity structure model and signalling through cell surface mechanoreceptors including ECM binding molecules. The tensegrity structure model postulates that a cell maintains a level of prestress generated actively by the actin microfilaments and intermediate filaments (68). This active stress element is balanced by structures resisting compression, mainly microtubules within the cell and components of the ECM. Matrix remodelling in response to mechanical forces is an adaptive response to maintain tensegrity in mechanosensitive tissues including cartilage and lung. In-vivo and in-vitro observations demonstrate that mechanical stimulation is necessary to maintain optimal cartilage and lung structure and function (81; 81; 91; 103). Thus mechanical forces regulate ECM composition which, in turn, will modify the mechanical microenvironment in tissues in a mutually reciprocal manner. This aspect provided a valuable tool for investigating biological functions in vitro.

Extracellular Matrix Catabolism and Anabolism

The ECM provides structural support as well as biological signals to almost every organ in the body. In the lung, the ECM provides structural support and acts as an adhesive as well as a guiding cue for diverse biological processes. Collagens are the most abundant ECM component in the lung constituting 60-70% of lung interstitium followed by elastin and PGs and glycoproteins (96).

The ECM composition of organs varies between the different anatomical and structural sites.

Lung PGs have just recently begun to be characterised. Perlecan and what is thought to be bamacan have been found in all lung basement membranes (20; 74). Of the SLR-PGs, lumican has been shown to be predominant and mainly found in the ECM of vessel walls and to a lesser extent in airway walls and alveolar septa (22). Immunohistochemical studies have demonstrated the presence of biglycan in the peripheral lung, though in very small quantities, where it is associated with airway and blood vessel walls (9; 22; 24). Furthermore, biglycan was shown to be associated with the epithelial cell layer particularly during development. Decorin has been localized to the tracheal cartilage, surrounding blood vessels and airways, and interlobular septae (9). However, Western analyses have demonstrated that decorin expression in the lung parenchyma is undetectable (22). Similarly, it was shown in this study that fibromodulin expression is also undetectable; an observation confirmed by the undetectable mRNA levels for this PG by Westergren-Thorsson et al. (102). The large aggregating PG, aggrecan, is only found in tracheal cartilage associated with HA in a complex stabilized by the link protein (85). On the other hand, versican can be found in small quantities in the airway and blood vessel walls (29), associated with smooth muscle cells (97) and fibroblasts (54), and has been co-localized with elastin fibres (85). HA can be found in tracheal cartilage (85), basolateral surfaces of the bronchiolar epithelium and the adventitia of blood vessels and airways (34; 35). The HA receptor, CD44, is expressed mainly by airway epithelium and alveolar macrophages (57; 62). Syndecans have been reported to be heavily expressed by alveolar epithelial cells (69).

The Importance of the Extracellular Matrix in Disease

Awareness of extracellular matrix importance has been heightened by the recognition that it profoundly influences the biology of the cell and hence, both mechanically and biochemically, the physiology of the whole structure in which the cell is embedded. There may be a real lead to the development of a novel therapeutic intervention where part of the clinical presentation is precipitated by an imbalance in catabolism vs anabolism such as may be found in chronic obstructive pulmonary disease.

Chronic Obstructive Pulmonary Disease (COPD), comprising chronic bronchitis and emphysema, is a major cause of chronic morbidity and mortality throughout the world. In the UK, COPD is the fifth leading cause of death, causing 26,000 deaths and 240,000 hospital admissions annually. The cost to the National Health Service of the UK of COPD-related hospital admissions is in excess of £486 million annually (15). Further costs are incurred due to co-morbidity such as respiratory infections and depression. Research into emphysema pathology and its treatment has been largely neglected because of the view that it is mainly self-inflected. Therefore strategies to effectively manage emphysema are needed in parallel to health promotion.

The Pathology of COPD

COPD is characterised by a progressive and irreversible airflow limitation (95) as a result of small airway disease (obstructive bronchiolitis) and parenchymal destruction (emphysema). Destruction of lung parenchyma is characterised by the loss of alveolar attachments to the small airways, decreased lung elastic recoil and as a consequence diminished ability of the airways to remain open during expiration (8).

Although the main risk factor for COPD is tobacco smoking, other predisposing factors have been identified (86). Emphysema is caused by inflammation, an imbalance of proteinases and antiproteinases in the lung (typified by hereditary $\alpha$-1 antitrypsin deficiency) and oxidative stress which leads to the destruction of the ECM.

Current Treatments for COPD and Emphysema

To date, the only available drug treatments for COPD sufferers have focussed primarily on bronchodilation using anticholinergics and dual $\beta$2-dopamine2 receptor antagonists. Inflammation in COPD is resistant to corticosteroids. Metalloproteinase (MMP) inhibitors are currently being developed to treat COPD, although in their current formulation, serious toxic side effect are almost certain to limit their use. Retinoids have also been shown to induce alveolar repair though this remain largely disputed. However, notwithstanding all such hopeful activities, what is clearly lacking is an agent which may aid in the repair of injured ECM.

In summary, COPD/emphysema is a paradigm for diseases which have a strong element of ECM remodelling as a major contributor to their pathophysiology. Other organs which require tissue repair include, but are not limited to; skin, central nervous system, liver, kidney, cardiovascular system, bone and cartilage. Furthermore, current therapeutics have focused primarily on preventative or symptom-relieving treatments. However, due to the progressive nature of both diseases together with often late diagnosis, regaining normal function remains a problem.

Recently, novel therapeutic approaches targeting integrin function have been adopted. Very late antigen-4 (VLA4) or $\alpha$4 integrin antagonists are currently in advance stages of trials for the treatment of asthma, multiple sclerosis and Crohn's disease (58; 60; 71). Antagonists to $\alpha v \beta 3$ integrin have attenuated adjuvant-induced arthritis and now are undergoing trials (6). The target of the functional blocking or antagonism is attenuating inflammation and this has not been demonstrated to affect the ECM alteration usually associated with those conditions.

The inventors have now surprisingly shown that compounds which modulate the function of beta 1 integrin facilitate improved tissue repair and regeneration.

SUMMARY OF THE INVENTION

According to the present invention there is provided a method of promoting tissue repair, the method comprising the step of administering a compound which modulates the function of beta 1 integrin.

Preferably the compound functionally modulates the activity of the beta 1 integrin. Without being bound by theory, the inventors theorise that the modulation of the beta 1 integrin which results from binding can result in an alteration of the metalloproteinase (MMP) balance, and/or inhibiting the apoptotic pathway and related intracellular apoptotic activity and signalling.

'Modification' or 'modulation' includes a change in the function of, or the shedding of the $\beta 1$ integrin.

It is thought that a compound according to the present invention may also act by shedding the $\beta 1$ integrin and/or affecting MMPs/TIMPs balance, as described above. Further the compound may affect the apoptotic pathway.

As used herein, the term 'tissue repair' relates to repair or regeneration of tissue following damage or trauma.

The discovery that modulation of the beta 1 integrin may be useful in tissue repair enables the provision of further novel compounds useful for tissue repair.

Accordingly, a further aspect of the invention provides a method of screening compounds for use in tissue repair, the method including the step of determining the ability of a compound to modify or modulate the function of the beta 1 integrin.

Preferably the method includes the step of determining the ability of a compound to bind the domain corresponding to residues 82-87 of the mature beta 1 (β1) integrin. These residues have the sequence as defined in SEQ ID NO:1, namely TAEKLK (Threonine-Alanine-Glutamic Acid-Lysine-Leucine-Lysine).

A yet further aspect of the present invention provides novel compounds identified from the assay methods described herein which modulate the function of beta 1 integrin.

The novel compounds of the present invention can be used in tissue repair in any tissue, for example tissue of the lung, skin, liver, kidney, nervous system, cartilage, bone and cardiovascular system.

In one embodiment the novel compounds binds the beta 1 integrin molecule at amino acid sequence corresponding to residues 82-87 of the mature beta 1 (β1) integrin molecule. It is to be understood, however, that this is not limiting and there are other domains in the β1 integrin molecule to which compounds may bind.

In the known sequence, residues 82-87 are the residues of the sequence identified by the nomenclature SEQ ID NO 1: TAEKLK (Threonine-Alanine-Glutamic Acid-Lysine-Leucine-Lysine).

The compound may be a peptide or an analogue thereof or alternatively be a chemical. The compound may further be a synthetic peptide or a synthetic chemical.

In a preferred embodiment the compound is an antibody.

The antibody is preferably a humanised antibody.

The antibody may be a chimeric antibody.

Alternatively the antibody could be a human antibody.

In one embodiment the antibody may be based on or derived from the functional modifying antibody of β1 integrin obtainable as produced by a commercial clone JB1a from Chemicon (this antibody may also be known as J10).

In a further embodiment the antibody could be based on or derived from the antibody 6S6. 6SS targets a domain of the β1 integrin yet to be specifically identified, but thought to be in the EGF-like repeat domain distinct from the 82-87 domain of the mature β1 integrin molecule targeted by the JB1a antibody.

A yet further aspect of the present invention provides a method of improving tissue repair and regeneration, the method including the steps of:
    selecting a composition including a compound capable of binding to beta 1 integrin or an analogue thereof,
    administering a therapeutically useful amount of the composition to a subject in need of treatment.

Preferably a therapeutically useful amount of the composition results in the binding of beta 1 integrin such that its activity is modulated and tissue repair and regeneration results.

A yet further aspect of the present invention provides for a compound which modulates the function of beta 1 integrin for use in tissue repair.

Such compounds may be used in the methods of the invention.

A yet further aspect of the present invention provides for the use of a compound which modulates the function of beta 1 integrin in the preparation of a medicament for the repair of tissue.

The invention further provides the use of an antibody to beta 1 integrin in the preparation of a medicament for the treatment of injured tissue administered via any therapeutic route.

DETAILED DESCRIPTION

Treatment

The term 'treatment' as used herein refers to any regime that can benefit a human or non-human animal. The treatment may be in respect of an existing condition or may be prophylactic (preventative treatment). Treatment may include curative, alleviation or prophylactic effects.

Antibodies

An "antibody" is an immunoglobulin, whether natural or partly or wholly synthetically produced. The term also covers any polypeptide, protein or peptide having a binding domain that is, or is homologous to, an antibody binding domain and in particular the antibody binding domains of the beta 1 integrin to which the Jb1a antibody or 6SS antibody binds. Such polypeptides, proteins or peptides can be derived from natural sources, or they may be partly or wholly synthetically produced. Examples of antibodies are the immunoglobulin isotypes and their isotypic subclasses and fragments which comprise an antigen binding domain.

Antibodies for use in the invention, including for example the Jb1a or 6S6 antibodies or analogues thereof.

Analogues of such antibodies may be made by varying the amino acid sequence of the antibody e.g. by manipulation of the nucleic acid encoding the protein or by altering the protein itself. Such derivatives of the amino acid sequence may involve insertion, addition, deletion and/or substitution of one or more amino acids Preferably such analogues involve the insertion, addition, deletion and/or substitution of 5 or fewer, and most preferably of only 1 or 2 amino acids.

Analogues also include derivatives of the peptide sequences of the antibodies, including the peptide being linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

Analogues of and for use in the invention preferably retain beta 1 integrin modulating activity.

Antibodies for use in the invention may be monoclonal or polyclonal, or fragments thereof. The constant region of the antibody may be of any class including, but not limited to, human classes IgG, IgA, IgM, IgD and IgE. The antibody may belong to any sub class e.g. IgG1, IgG2, IgG3 and IgG4.

The term "antibody" includes antibodies which have been "humanised". Methods for making humanised antibodies are known in the art. Such methods are described, for example, in Winter, U.S. Pat. No. 5,225,539. A humanised antibody may be a modified antibody having the hypervariable region of a monoclonal antibody and the constant region of a human antibody. Thus the binding member may comprise a human constant region.

As antibodies can be modified in a number of ways, the term "antibody" should be construed as covering any binding member or substance having a binding domain with the required specificity. Thus, this term also covers antibody fragments, derivatives, functional equivalents and homologues of antibodies, including any polypeptide comprising an immunoglobulin-binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of antigen binding.

Examples of such binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (99) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (11; 50); (viii) bispecific single chain Fv dimers (PCT/US92/09965) and (ix) "diabodies", multivalent or multispecific fragments constructed by gene fusion (WO94/13804; (46)).

Substitutions may be made to the binding epitope of antibodies for use in the invention for example amino acid residues may be substituted with a residues of the same or similar chemical class, and which result in no substantial conformational change of the binding epitope.

Antibodies of and for use in the invention can be prepared according to standard techniques. Procedures for immunising animals, e.g. mice with proteins and selection of hybridomas producing immunogen specific monoclonal antibodies are well known in the art. The antibody is preferably a monoclonal antibody.

Pharmaceutical Compositions

The present invention further extends to pharmaceuticals and to pharmaceutical compositions for the modulation of the function of the beta 1 integrin.

Accordingly, yet further aspect of the present invention provides a pharmaceutical composition for use in tissue repair wherein the composition includes as an active ingredient, a compound which modifies the function of beta 1 integrin.

Pharmaceutical compositions according to the present invention, and for use in accordance with the present invention may comprise, in addition to active ingredient, a pharmaceutically acceptable excipient, carrier, buffer stabiliser or other materials well known to those skilled in the art.

Such materials should be non-toxic and should not interfere with the efficacy of the active ingredient. The precise nature of the carrier or other material will depend on the route of administration.

Dose

The composition is preferably administered to an individual in a "therapeutically effective amount", this being sufficient to show benefit to the individual. The actual amount administered, and rate and time-course of administration, will depend on the individual and condition being treated.

The optimal dose can be determined based on a number of parameters including, for example the age of the individual and the extent of tissue damage, the precise form of the composition being administered and the route of administration.

The composition may be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7th Edition ISBN 0-683305-72-7 the entire disclosures of which is herein incorporated by reference.

Assays

As described above, the invention provides assay systems and screening methods for determining compounds which may be used in tissue repair. As used herein, an "assay system" encompasses all the components required for performing and analysing results of an assay that detects and/or measures a particular event or events.

A variety of assays are available to detect the activity of compounds such as antibodies, peptides and chemicals which have specific binding activity to beta 1 integrin.

The precise format of the assay(s) of the invention may be varied by those skilled in the art using routine skill and knowledge.

Preferred screening assays are high throughput or ultra high throughput and thus provide automated, cost-effective means of screening.

The discovery that modifications of beta 1 integrin may be useful in tissue repair enables the indentification and of further novel compounds useful for tissue repair.

Accordingly, a further aspect of the invention provides an assay for identifying compounds suitable for use in tissue repair, said assay comprising the steps of:
  providing a candidate compound,
  bringing the candidate compound into contact with beta 1 integrin or an analogue thereof,
  determining the presence or absence of modulation of beta 1 integrin activity by the candidate compound,
wherein modulation of beta 1 integrin activity is indicative of utility of that compound in tissue repair.

Preferably the method includes the step of determining the ability of a compound to bind the domain corresponding to residues 82-87 of the mature beta 1 (β1) integrin. These residues have the sequence as defined in SEQ ID No:1, namely TAEKLK (Threonine-Alanine-Glutamic Acid-Lysine-Leucine-Lysine).

In another embodiment, the presence or absence of beta 1 integrin activity is assessed by monitoring modulation of MMP activity.

Beta 1 integrin modulating activity may be assessed in the assays of the invention using any suitable means. For example, the effect of the agent on MMP levels or balance, and/or the effect on apoptosis and apoptotic pathways. Exemplary assays are western blotting analyses and ELISA based assays for MMPs protein in both active and inactive forms, proteoglycans synthesis using western analyses and ELISA based assays, cell adhesion based assays, apoptosis assays using in-situ labelling, immunohistochemistry and gel analyses.

In various further aspects, the present invention relates to screening and assay methods and to substances identified thereby.

Novel compounds identified using the assays of the invention form a further independent aspect of the invention.

In assays of the invention, analogues of beta 1 integrin may be used. Such analogues may comprise one or more binding sites of beta 1 integrin, for example the binding site corresponding to amino acid residues 82 to 87 of the mature beta 1 integrin molecule. Alternatively, the analogue may comprise a beta 1 integrin mimetic. The skilled person is well aware of how to design such a mimetic. Briefly, a template molecule is selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the beta 1 integrin.

The mimetic found by this approach can then be used in assays of the invention in place of beta 1 integrin to see whether they have a target property eg. beta 1 integrin activity, or to what extent they exhibit it. Further optimisation or modification can then be carried out to arrive at one or more final mimetics for in-vivo or clinical testing or for use in the assays of the invention.

Preferred features of each aspect of the invention are as for each other aspect, mutatis mutandis, unless the context demands otherwise.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

Figure 2:
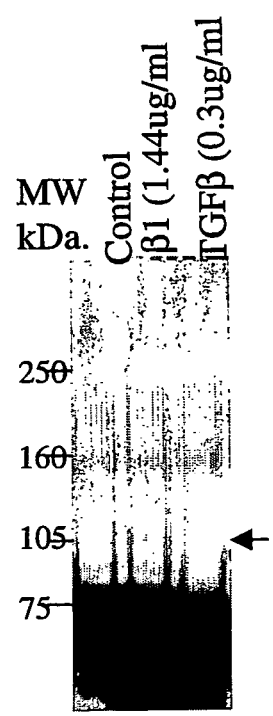
Figure 11:
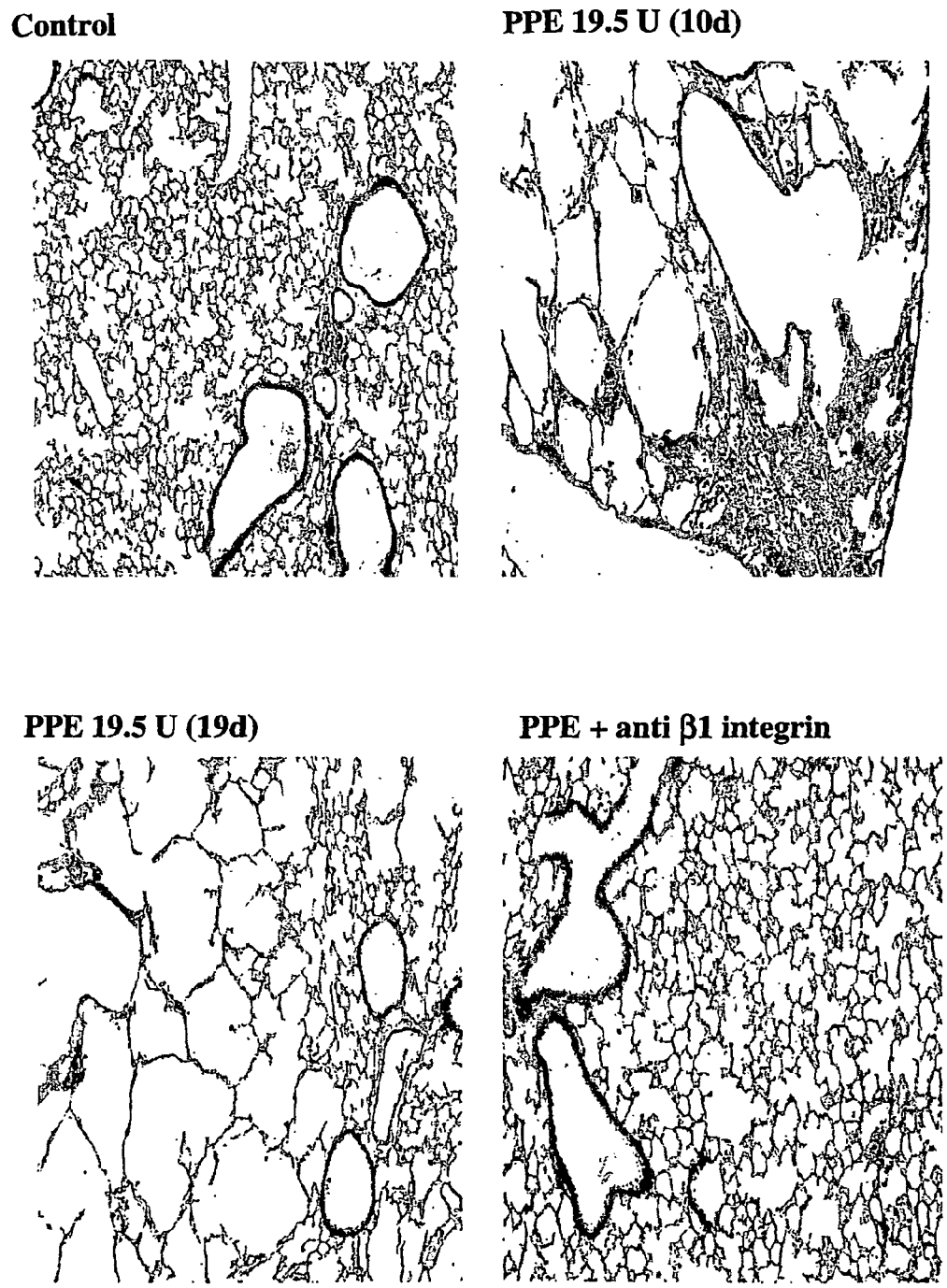
Figure 15:
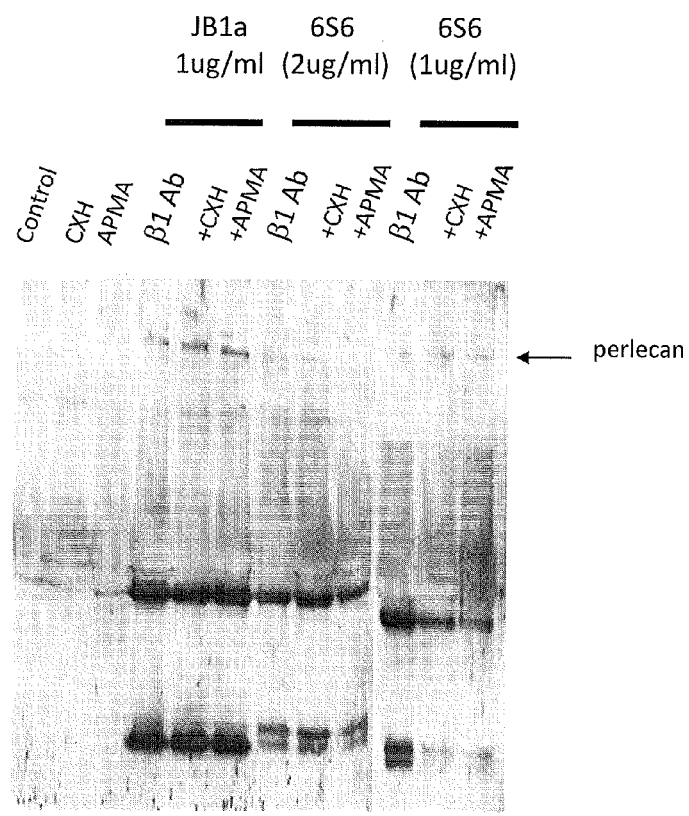
Figure 16:
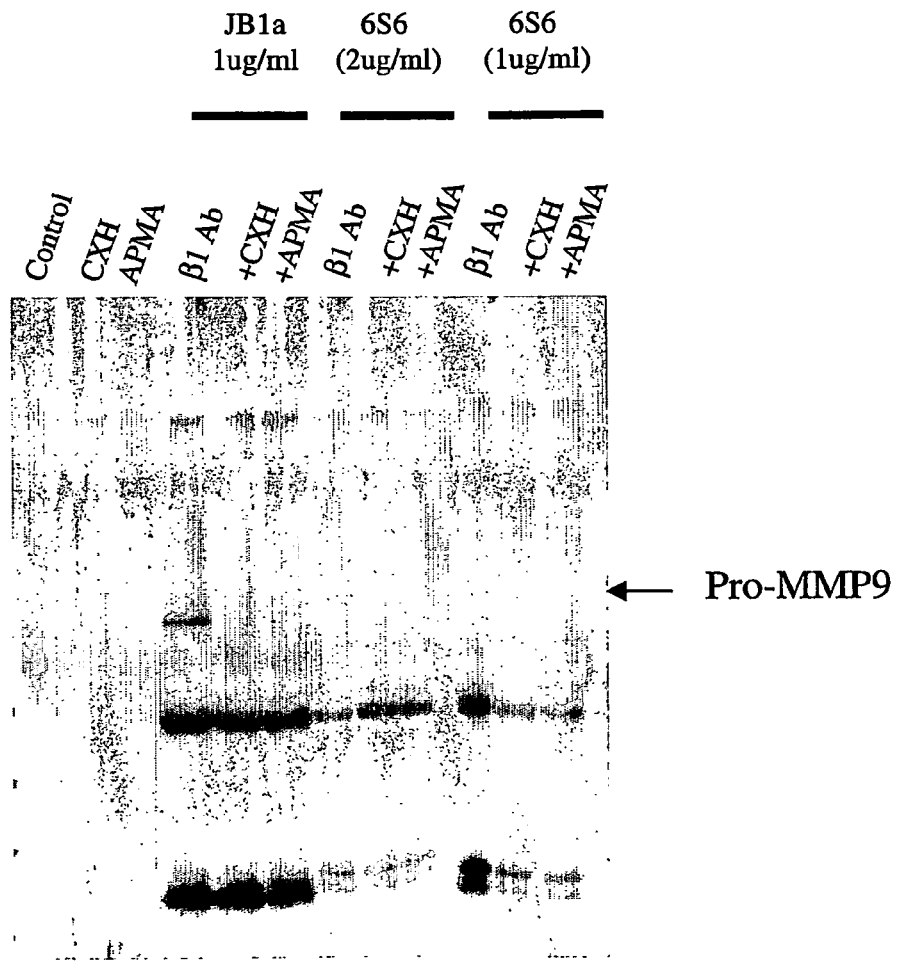
Figure 17:
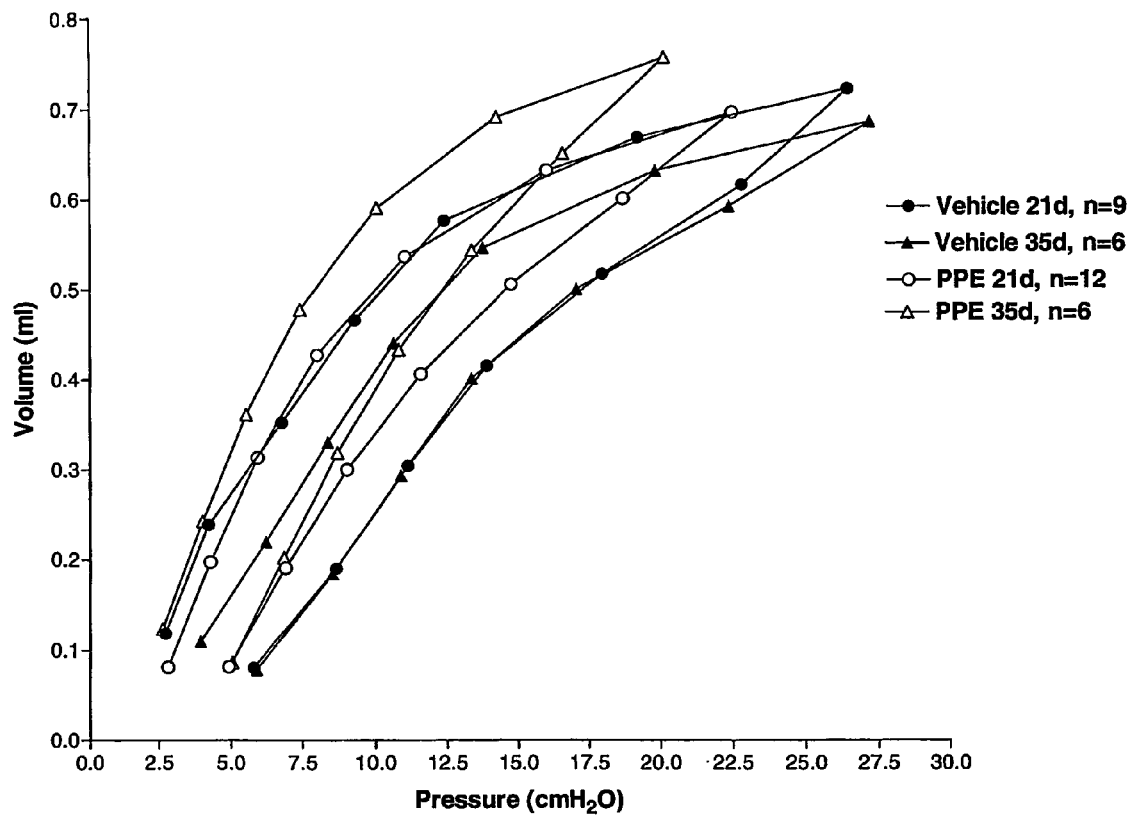
Figure 18:
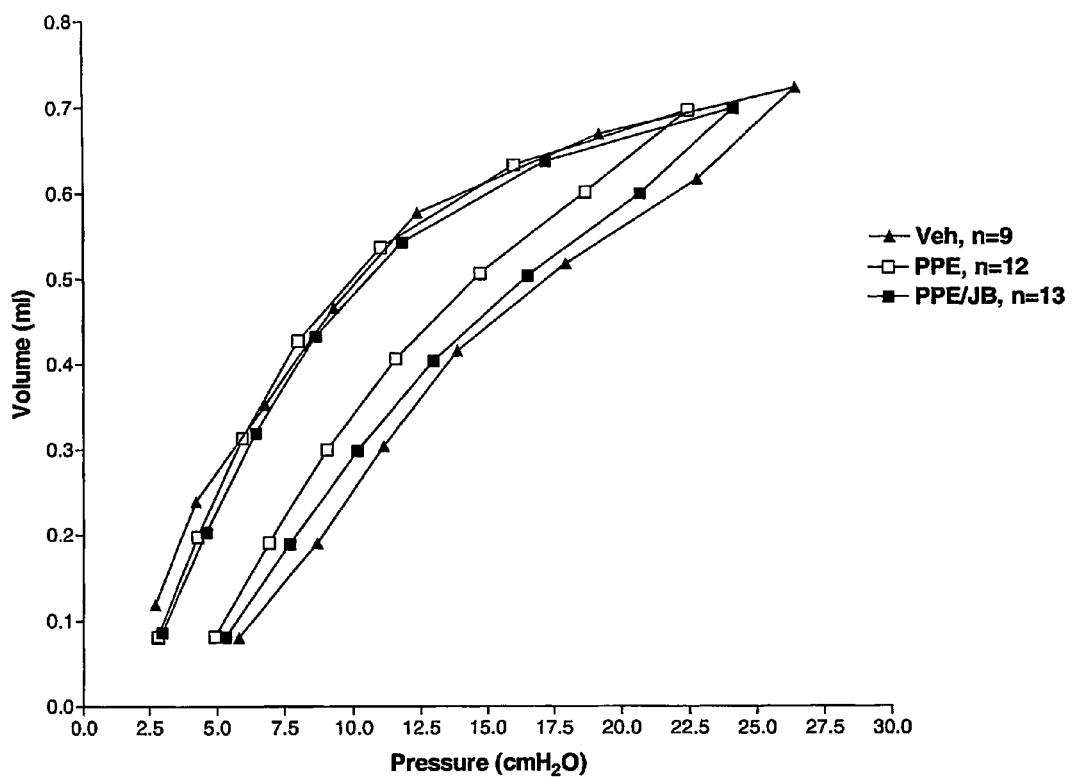
Figure 19:
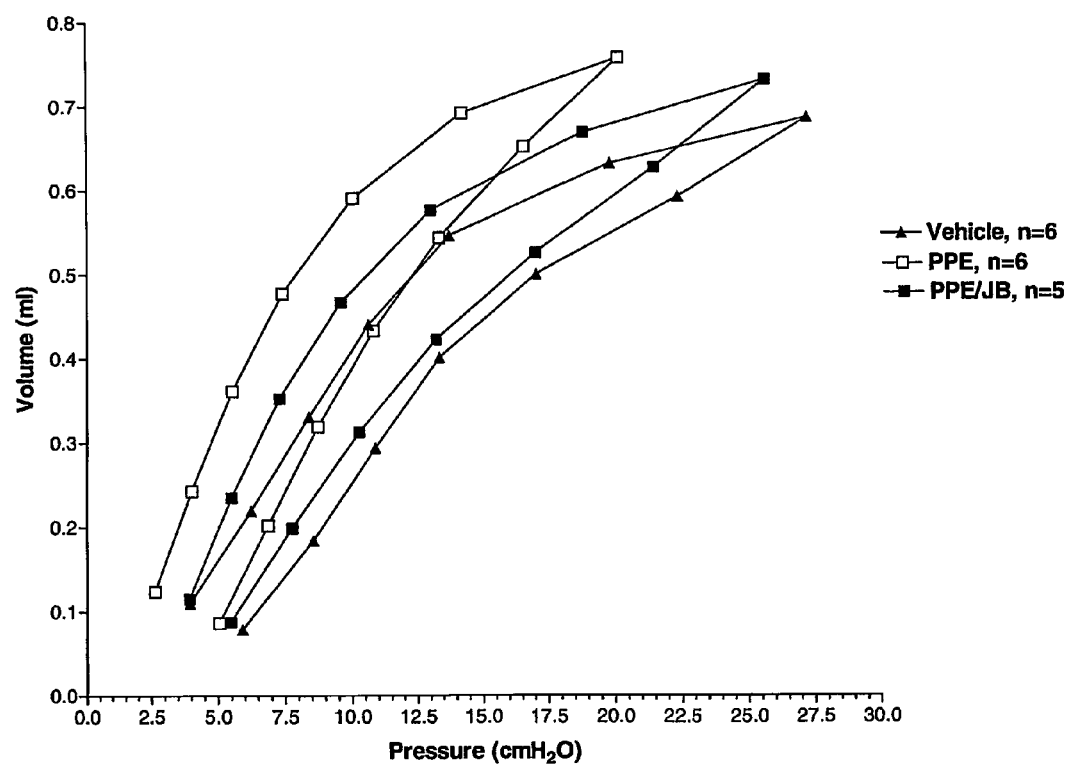
Figure 20:
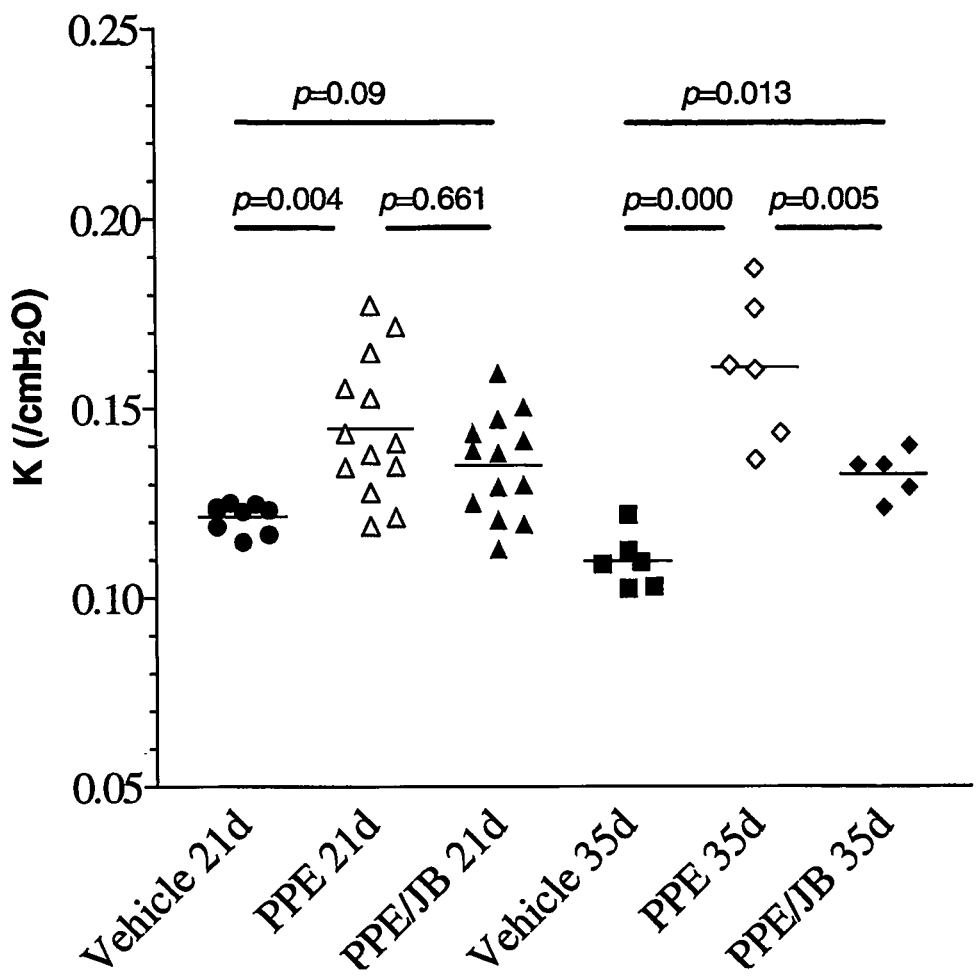
Figure 21:
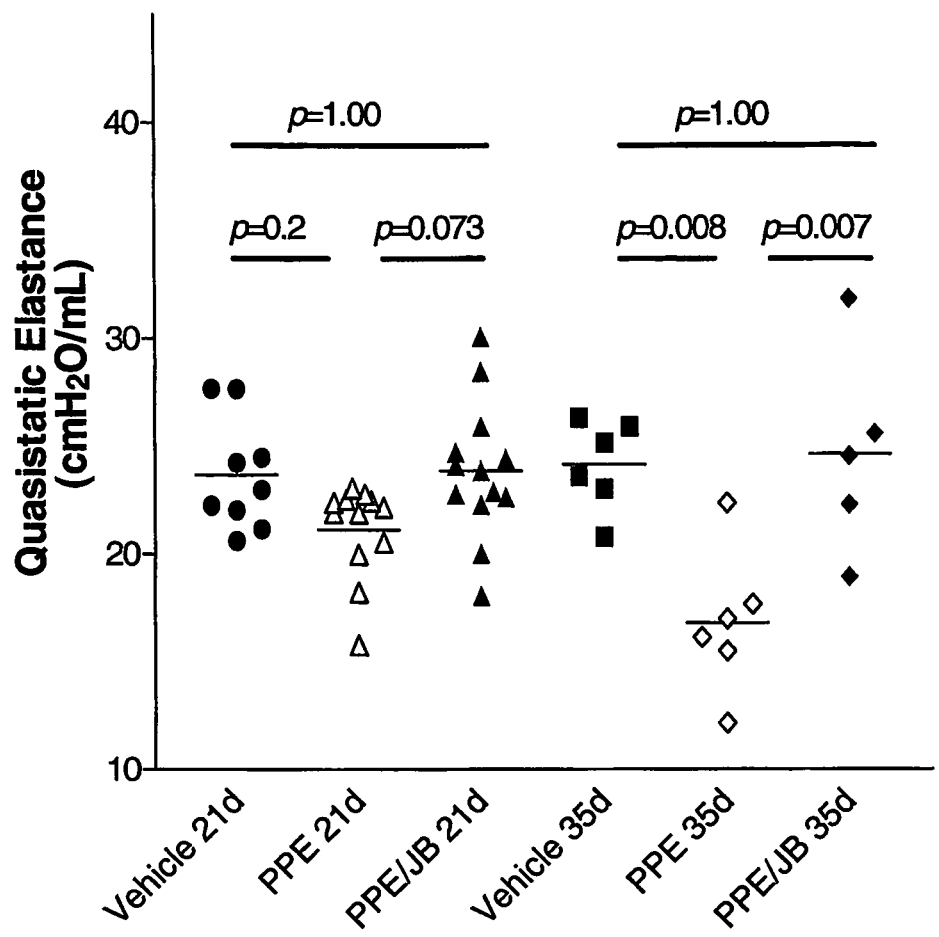
Figure 22:
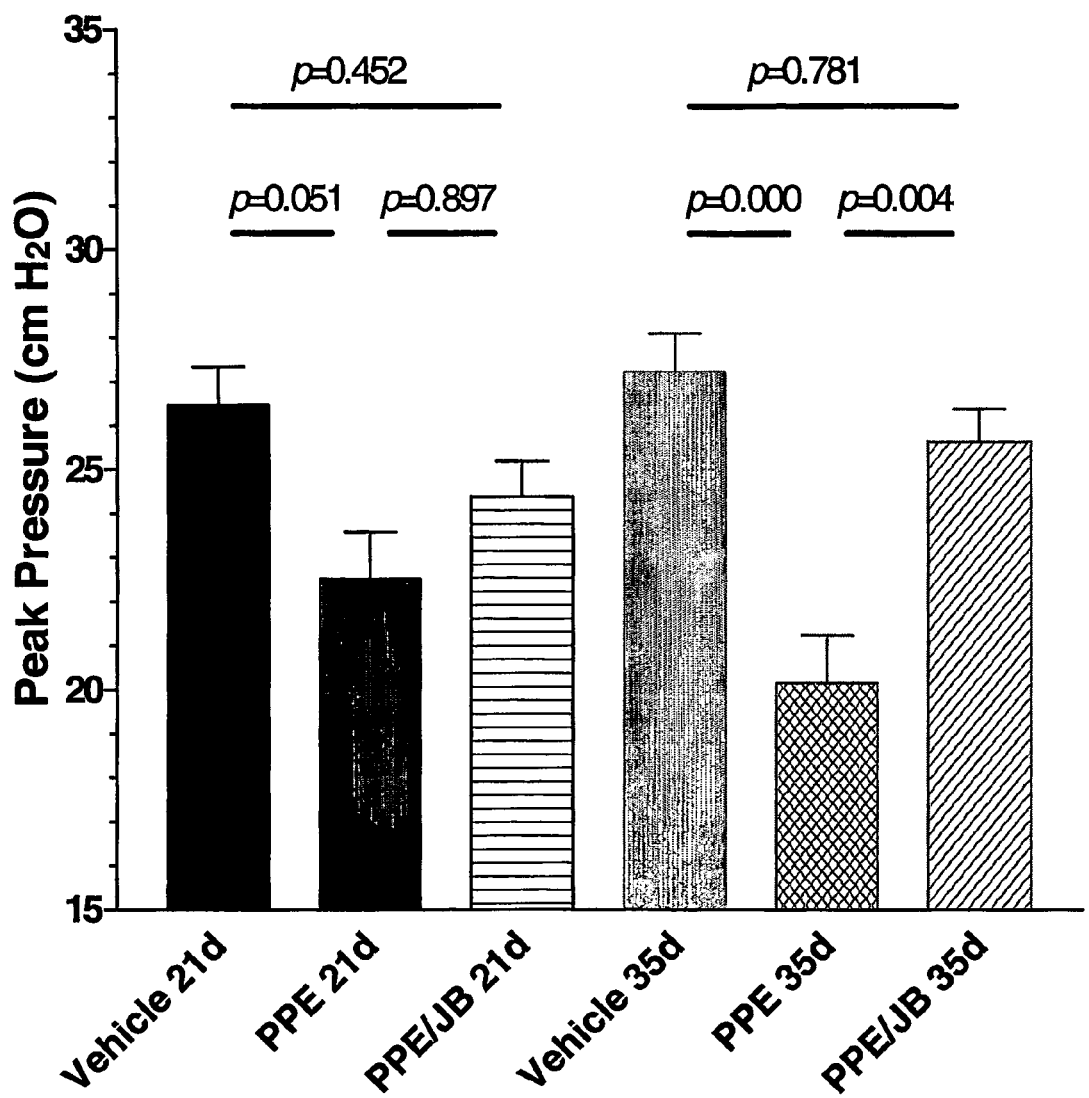
Figure 23:
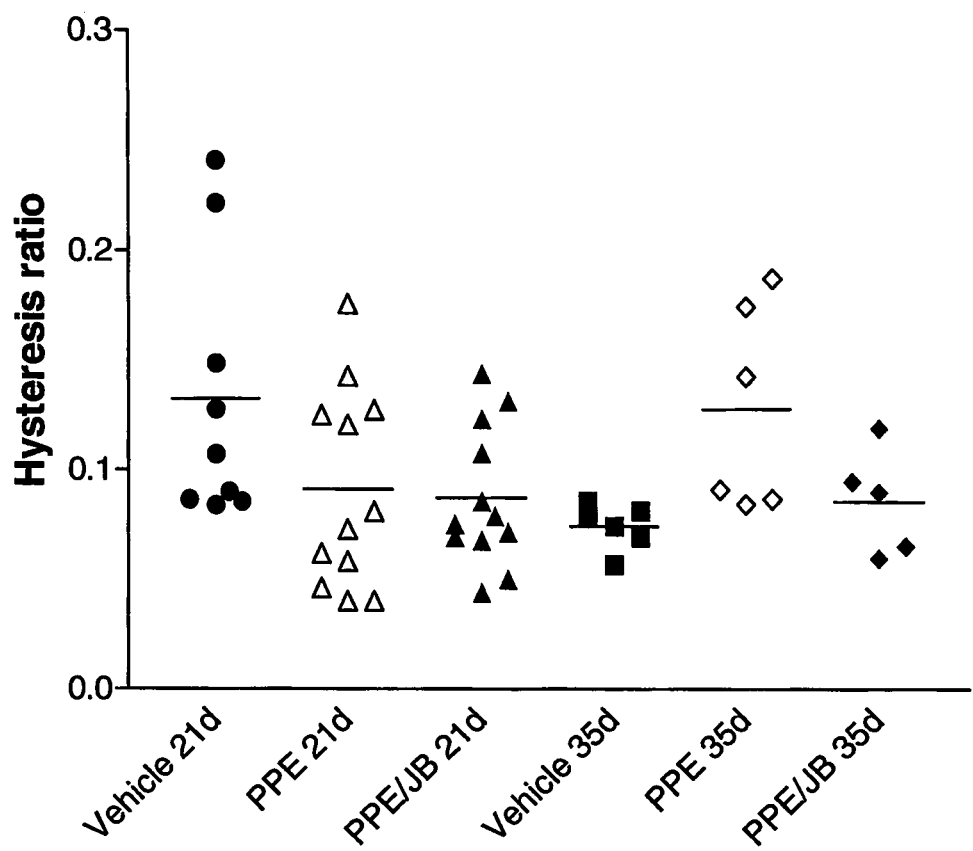
Figure 24:
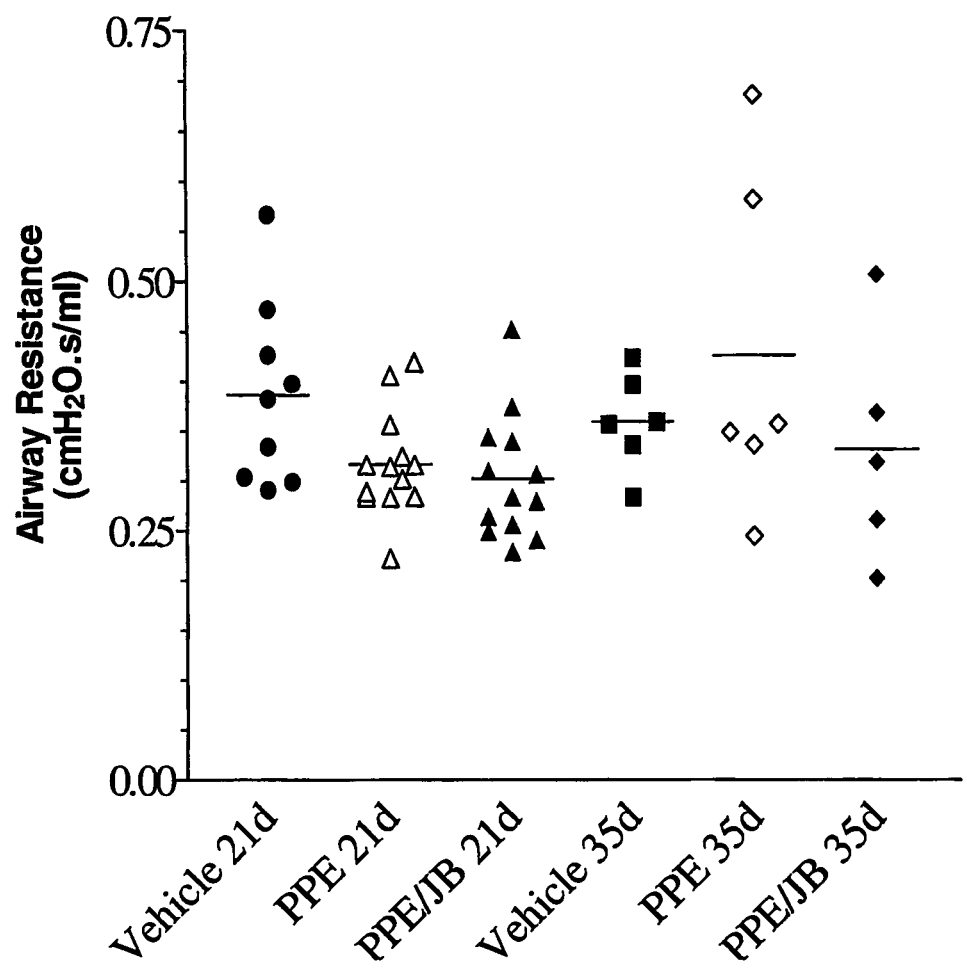
Figure 25:
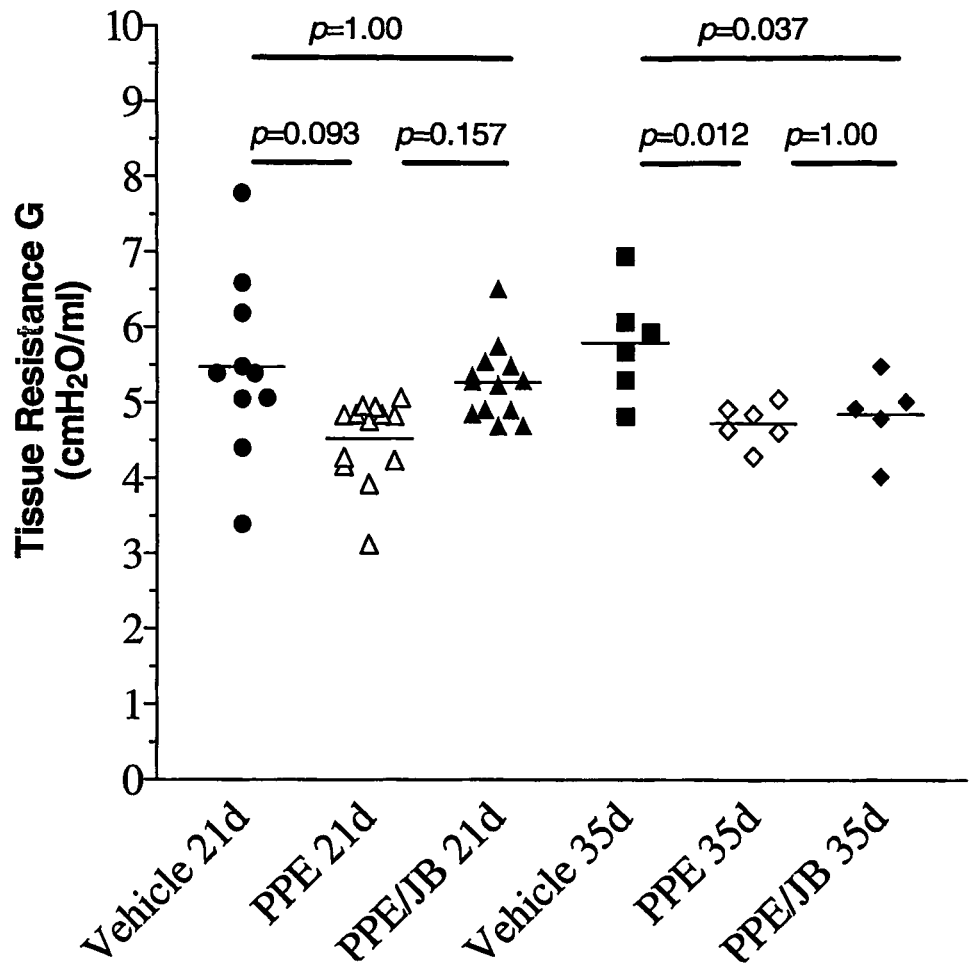
Figure 26:
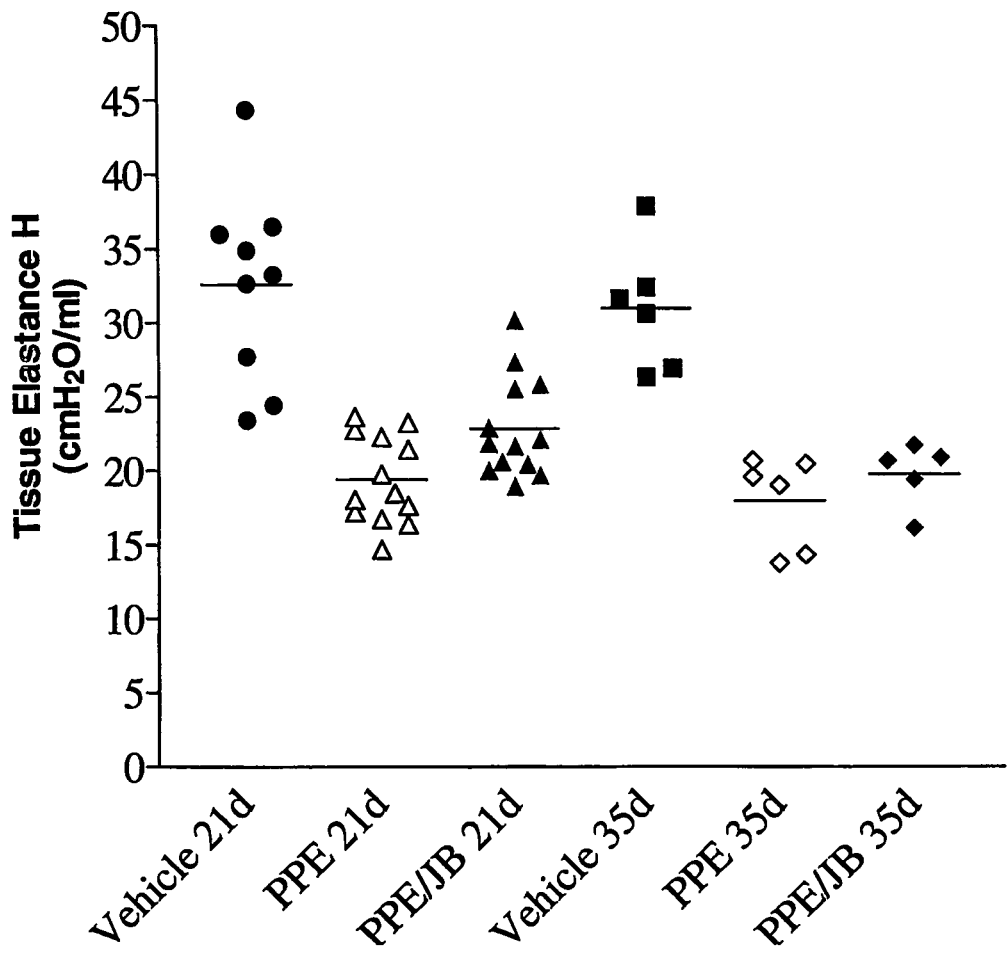
Figure 27:
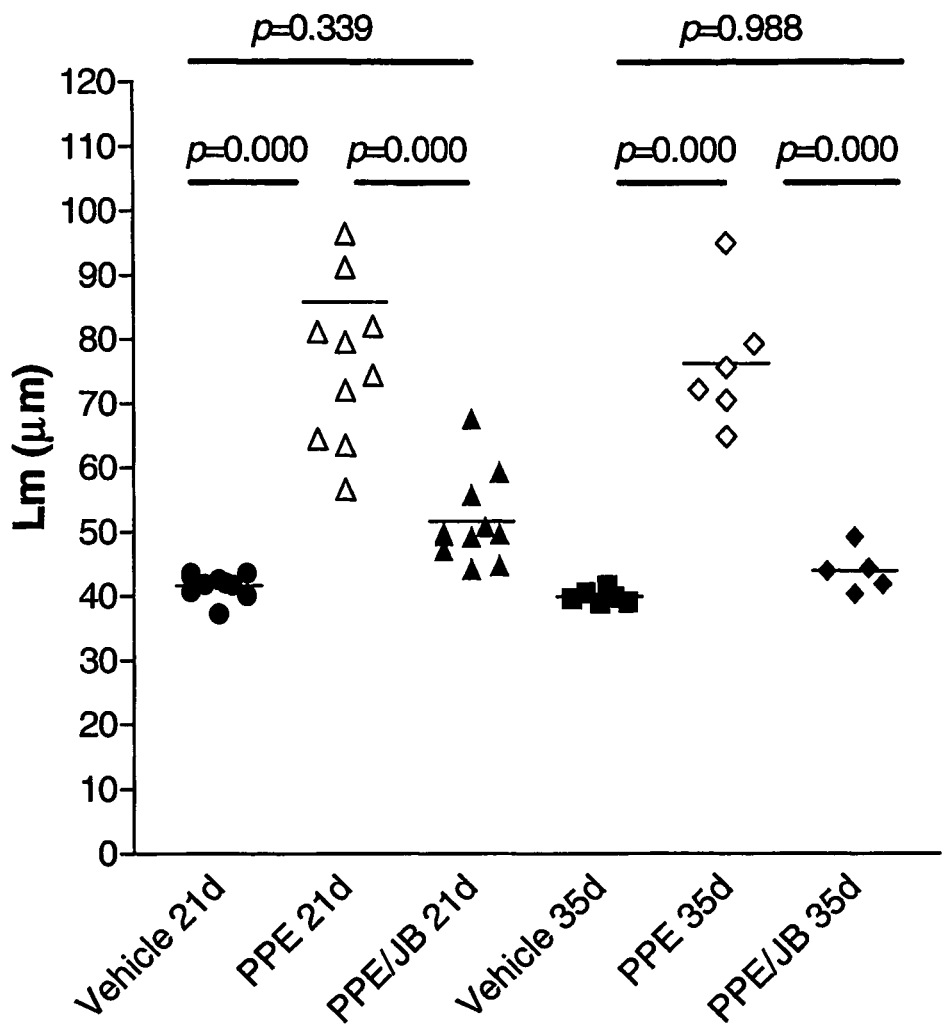
Figure 28:
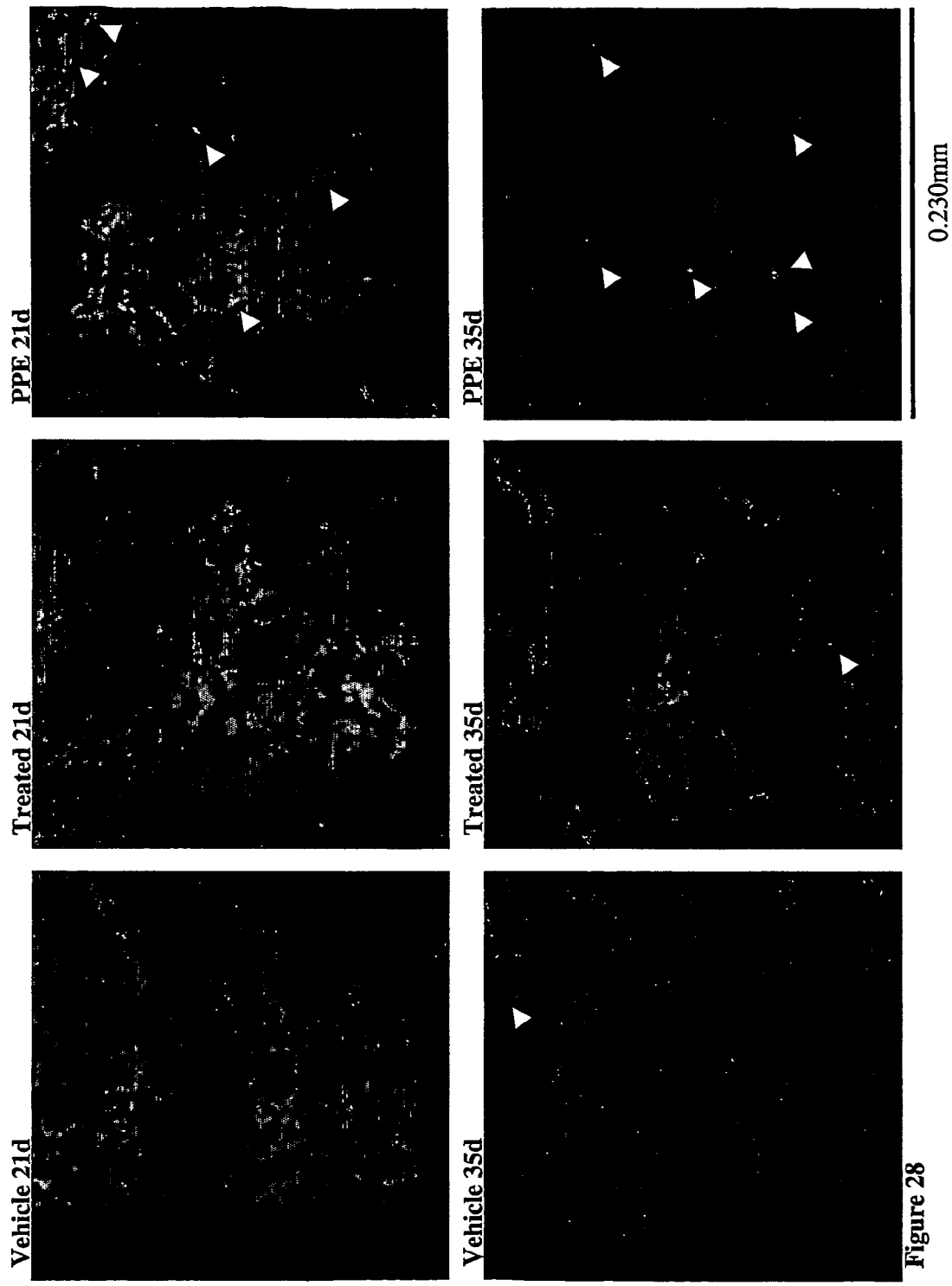
Figure 29:
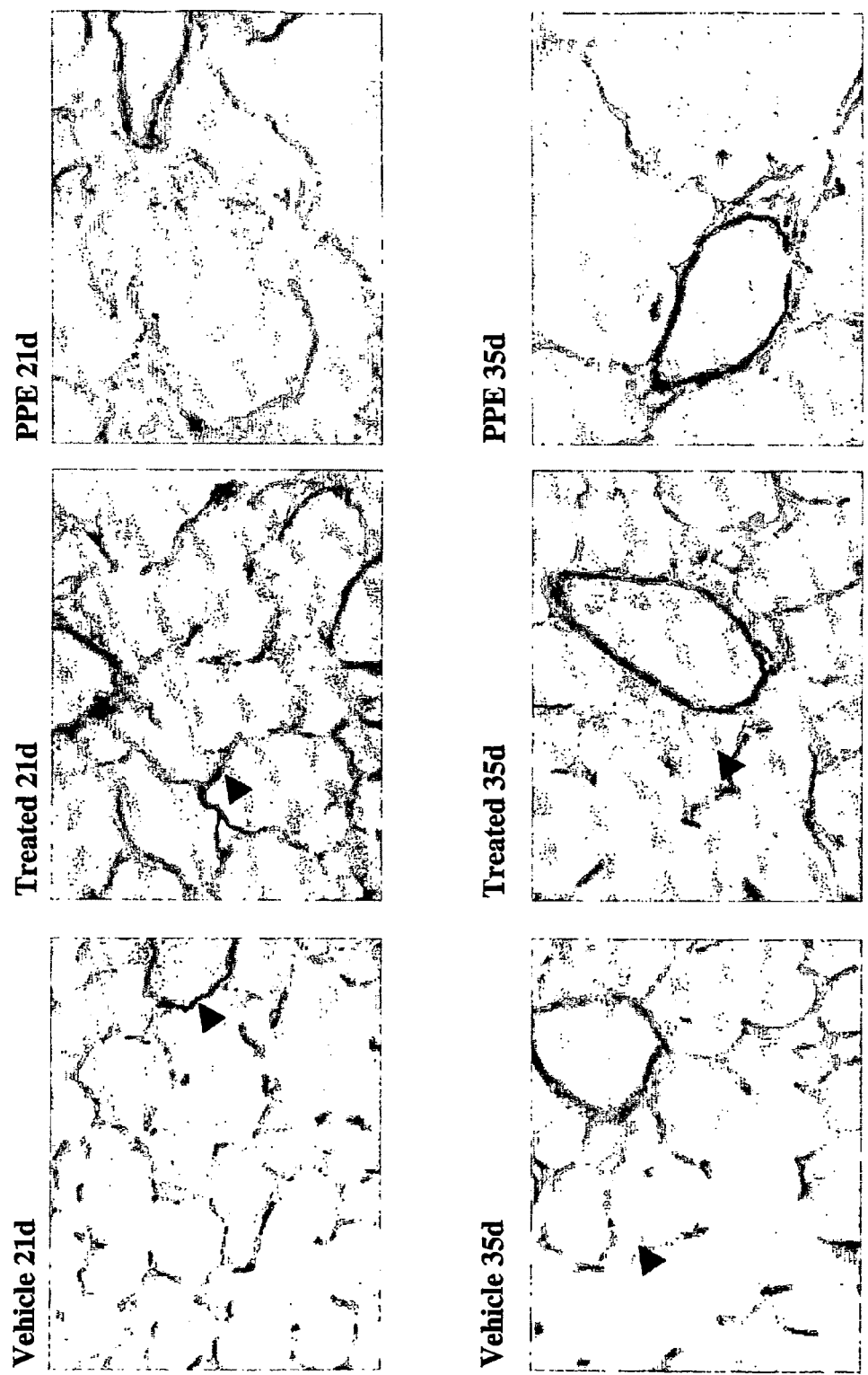

The invention is exemplified herein with reference to the following non limiting examples which are provided for the purpose of illustration and are not to be construed as being limiting on the present invention. Further reference is made to the accompanying figures wherein;

FIG. 1 illustrates time-dependent effects of functional modification of $\beta 1$ integrin and neutralising TGF-$\beta$ on ECM PG from H441 cell lines, FIG. 2 shows the presence of a 110 kDa $\beta 1$ integrin in the media of chondrocytes in alginate cultures and H441 cells separated onto 6% SDS-polyacrylamide gels following $\beta 1$ integrin function modulation, FIG. 3 illustrates the time-dependent effect of functional modification of $\beta 1$ integrin on ECM PGs in human lung explants and the lack of effect using a control $\beta 1$ integrin antibody, FIG. 4 illustrates the effects of functional modification of $\beta 1$ integrin on ECM PGs in human lung explants, FIG. 5 shows Western analyses demonstrating the increase in inactive MMP9 in the media of human lung explants following $\beta 1$ integrin function modulation, FIG. 6 shows Western analyses demonstrating the increase in ECM PG, perlecan in the media of cultured human lung cells (Collagenase digest alone or in co-culture with the Elastase digests) following $\beta 1$ integrin function modulation ($\beta 1$ Ab). The figure also shows the effect of cycloheximide (CXH) and APMA on the PG response to $\beta 1$ integrin function modulation. In addition, the effect of neutralising MMP7 and 9 and MMPs are demonstrated, FIG. 7 shows Western analyses demonstrating the increase in TIMP1 in the media of cultured human lung cells (Collagenase digest alone or in co-culture with the Elastase digests) following $\beta 1$ integrin function modulation ($\beta 1$ Ab). The figure also shows the effect of cycloheximide (CXH) and APMA on the TIMP1 response to $\beta 1$ integrin function modulation. In addition, the effect of neutralising MMP7 and 9 and MMPs are demonstrated, FIG. 8 shows Western analyses demonstrating the decrease in MMP1 in the media of cultured human lung cells (Collagenase digest alone or in co-culture with the Elastase digests) following $\beta 1$ integrin function modulation ($\beta 1$ Ab). The figure also shows the effect of cycloheximide (CXH) and APMA on the TIMP1 response to $\beta 1$ integrin function modulation. In addition, the effect of neutralising MMP7 and 9 and MMPs are demonstrated, FIG. 9 shows Western analyses demonstrating the increase in inactive MMP9 in the media of cultured human lung cells (Collagenase digest alone or in co-culture with the Elastase digests) following $\beta 1$ integrin function modulation ($\beta 1$ Ab). The figure also shows the effect of cycloheximide (CXH) and APMA on the TIMP1 response to $\beta 1$ integrin function modulation. In addition, the effect of neutralising MMP7 and 9 and MMPs are demonstrated, FIG. 10 shows a photograph demonstrating the effect of $\beta 1$ integrin functional modification on the size lungs of emphysematous mice (PPE), FIG. 11 shows haematoxylin and eosin staining of 4 um formalin-fixed paraffin embedded section demonstrating the effect of $\beta 1$ integrin functional modification on repair of lung architecture in elastase-induced emphysema in mice, FIG. 12 demonstrates the effect of $\beta 1$ integrin functional modification on air space enlargement in Elastase induced emphysema in mice, FIG. 13 demonstrates the effect of $\beta 1$ integrin functional modification on active TGF$\beta 1$ levels in the bronchoalveolar lavage fluid in Elastase induced emphysema in mice, FIG. 14 demonstrates the correlation of active TGF$\beta 1$ levels in the bronchoalveolar lavage fluid and air space enlargement index and the effect of $\beta 1$ integrin functional modification in Elastase induced emphysema in mice, FIG. 15 shows Western analyses demonstrating the increase in ECM PG, perlecan in the media of cultured human lung cells (NCI-H441) following $\beta 1$ integrin function modulation ($\beta 1$ Ab). 6S6 anti $\beta 1$ integrin antibody was also used. The figure also shows the effect of cycloheximide (CXH) and APMA on the PG response to $\beta 1$ integrin function modulation, FIG. 16 shows Western analyses demonstrating the increase in inactive MMP9 in the media of cultured human lung cells (NCI-H441) following $\beta 1$ integrin function modulation ($\beta 1$ Ab). 6S6 anti $\beta 1$ integrin antibody was also used. The figure also shows the effect of cycloheximide (CXH) and APMA on the PG response to $\beta 1$ integrin function modulation, FIG. 17 shows the time course effect of porcine pancreatic elastase (PPE) instillation in mice on the pressure-volume curves of the respiratory system, FIG. 18 shows the effect of $\beta 1$ integrin function modulation on the reversal of PPE effect on the pressure-volume characteristics in mice instilled intratracheally with PPE and treated using JB1a antibody at day 14 then terminated at day 21, FIG. 19 shows the effect of $\beta 1$ integrin function modulation on the reversal of PPE effect on the pressure-volume characteristics in mice instilled intratracheally with PPE and treated using JB1a antibody at day 21 and 28 then terminated at day 35, FIG. 20 shows the effect of $\beta 1$ integrin function modulation on the reversal of PPE effect on the curvature of the upper part of the pressure-volume (K) in mice instilled intratracheally with PPE and treated using JB1a antibody at day 14 then terminated at day 21 (21 d) or at day 21 and 28 then terminated at day 35 (35 d), FIG. 21 shows the effect of β1 integrin function modulation on the reversal of PPE effect on quasi-static elastance at 5-13 cmH$_2$O pressure in mice instilled intratracheally with PPE and treated using JB1a antibody at day 14 then terminated at day 21 (21 d) or at day 21 and 28 then terminated at day 35 (35 d), FIG. 22 shows the effect of β1 integrin function modulation on the reversal of PPE effect on the peak pressures obtained from the pressure-volume manoeuvres in mice instilled intratracheally with PPE and treated using JB1a antibody at day 14 then terminated at day 21 (21 d) or at day 21 and 28 then terminated at day 35 (35 d), FIG. 23 shows the effect of β1 integrin function modulation on the reversal of PPE effect on the quasi-static hysteresis in mice instilled intratracheally with PPE and treated using JB1a antibody at day 14 then terminated at day 21 (21 d) or at day 21 and 28 then terminated at day 35 (35 d), FIG. 24 shows the effect of β1 integrin function modulation on the reversal of PPE effect on Newtonian resistance (Raw, also known as airway resistance) in mice instilled intratracheally with PPE and treated using JB1a antibody at day 14 then terminated at day 21 (21 d) or at day 21 and 28 then terminated at day 35 (35 d), FIG. 25 shows the effect of β1 integrin function modulation on the reversal of PPE effect on tissue resistance (G) in mice instilled intratracheally with PPE and treated using JB1a antibody at day 14 then terminated at day 21 (21 d) or at day 21 and 28 then terminated at day 35 (35 d), FIG. 26 shows the effect of β1 integrin function modulation on the reversal of PPE effect on tissue elastance (H) in mice instilled intratracheally with PPE and treated using JB1a antibody at day 14 then terminated at day 21 (21 d) or at day 21 and 28 then terminated at day 35 (35 d), FIG. 27 shows the effect of β1 integrin function modulation on the reversal of PPE effect on air space enlargement using the mean linear intercept (Lm) in mice instilled intratracheally with PPE and treated using JB1a antibody at day 14 then terminated at day 21 (21 d) or at day 21 and 28 then terminated at day 35 (35 d), FIG. 28 shows immunohistochemical staining of 4 um formalin-fixed paraffin embedded section demonstrating the effect of β1 integrin functional modification on the reversal of PPE effects on apoptosis in the lungs of mice instilled intratracheally with PPE and treated using JB1a antibody at day 14 then terminated at day 21 (21 d) or at day 21 and 28 then terminated at day 35 (35 d). TUNEL positive cells (apoptotic) appear red (Rhodamine) are indicated with arrows. DAPI nuclear staining appears grey, FIG. 29 shows Resorcin-acid fuschin staining of 4 um formalin-fixed paraffin embedded section demonstrating the effect of β1 integrin functional modification on repair of elastic fibres after PPE-induce damage in the lungs of mice instilled intratracheally with PPE and treated using JB1a antibody at day 14 then terminated at day 21 (21 d) or at day 21 and 28 then terminated at day 35 (35 d), and FIG. 30, Table 1, shows the correlation coefficients (r) and the significance of the correlations between the lung physiological measurements and the mean linear intercept (Lm).

In a preliminary experiment, the present inventors attempted to investigate the role of the cell surface receptors in the synthesis of ECM which are altered in diseases such as COPD and are important for lung and cartilage function microscopically and macroscopically. The importance of those ECM molecules in health and disease is not exclusive to the lung.

The results described herein demonstrate that functional modification of β1 integrin through a domain corresponding to amino acid residues 82 to 87 and to a lesser extent through a domain not yet specifically identified, but thought to be in the EFG-like repeat domain distinct from the 82 to 87 domain, induces a substantial time- and dose-dependent increase in ECM in a human lung epithelial cell line (NCI-H441) in monolayer and human lung explants as well as human lung derived culture in monolayer or co-culture system. The response was observed using two different antibodies against β1 integrin though the magnitude of the response was variable. These domains are different from those previously described which bind to the amino acid sequence residues 207 to 218. It is also distinct from the known stimulatory domains which are localised to those amino acid residues and residues 657 to 670 and 671 to 703. Modulation of the cytokine TGF-β induced a less profound increase which was also time- and dose-dependent. This increase in all ECM PGs was sustained for extended periods of time without any additive doses.

These experiments demonstrate a novel finding which is that an increase in ECM can be achieved via the modulation of cell surface receptors and to a much lesser extent by modulating the binding of a soluble factor in a time- and dose-dependent manner in pulmonary derived cells and tissues in animal models. Potential, but non-binding mechanistic hypotheses are that this modulation may have led to alteration in the cell adhesion its damaged surroundings and thus prevented cell death permitting repair to ensue. This alteration in turn may affect the proteinase/antiproteinase balance which can be sequestered onto the surface of cells. Furthermore, the response could be a result of changes in gene transcription or translation. Our experiments have demonstrated that the response is due to combination of all the above. The ECM response to β1 integrin functional modification was accompanied by a decrease in cell death and increase in TIMP1, inactive MMP9 and active TGFβ1 and a decrease in MMP1.

When administered to animals which have emphysematous lungs, the treatment reversed the abnormal increase in the mean linear intercept (LM) as an index of air space enlargement, lung size and abnormal lung function as well as signs of inflammation. Furthermore, there was a decrease in cell death.

The potential of these findings lie in tissue repair in disease where the matrix is degraded and cannot be replenished as in diseases that include but not exclusive to COPD. The finding may offer a venue for therapeutic intervention in diseases where the only current lines of therapy focus on alleviating the symptoms by the use of anti-inflammatory agents but has no potential for regaining function. This could be achieved via the administration of humanised, chimeric or human antibodies or synthetic peptides or chemicals capable of binding β1 integrin and inhibiting cell death.

In summary, the results herein address a different potential therapeutic modality which focuses on increasing cell viability and ECM anabolism instead of decreasing catabolism.

Experimental Protocol

Human Lung Explants Culture and Human Lung Derived Cell Isolation

Human lung tissue specimens were obtained with consent and cultured as either 20-30 mg explant strips or cells.

Cell were isolated by sequential digestions modified from methods by Murphy et al. and Elbert et al. (25; 75) where the tissue (10 g) was washed using HEPES buffer (buffer A: 0.13M NaCl, 5.2 mM KCl, 10.6 mM Hepes, 2.6 mM Na$_2$HPO$_4$, 10 mM D-glucose, pH 7.4). The tissue was then incubated in 40 ml buffer A containing 0.855 mg Elastase (Roche) 0.5% trypsin, 200 U/g DNAsI, 1.9 mM CaCl$_2$, and 1.29 mM MgSO$_4$ for 40 minutes at 37° C.

The digest buffer is then aspirated and suspended cells washed three times in buffer A. The cells between each wash were pelleted by centrifuging the suspension for 10 minutes at 1100 rpm and 4° C. After the final was the cells were resuspended in buffer A, filtered through 40 um filter and then subjected to discontinuous Percoll gradient (1.089/1.04 g/ml). The cells were then plated onto multi-well culture plates and tissue culture transwells of 0.3 um pore size (Sigma) and maintained in culture using 1:1 DMEM/F12: Small airway growth media (Cambrex BioScince Wokingham Ltd.) containing 1% foetal calf serum L-glutamine and antibiotic/antimycotic/antifungal mixture and maintained at 5% in an $CO_2$ incubator.

The remaining tissue was treated with DMEM containing 40% foetal calf serum to inactivate the digestive enzymes and then washed using solution A. The tissue was then incubated in DMEM containing 1 mg/ml Collagenase, 0.5% trypsin and 200 U/g DNAsI and maintained at 5% in an $CO_2$ incubator. The cell suspension was washed as above and cells seeded on multiwell culture plates and maintained in DMEM (Sigma Aldrich) containing 10% foetal calf serum, L-glutamine and antibiotic/antimycotic/antifungal mixture and maintained at 5% in a $CO_2$ incubator.

Adenocarcinoma cell line derived from the lung were also used (H441) to test the effect of the antibodies on matrix synthesis. This cell line has epithelial type II characteristics.

Cultures were subjected to serum starving overnight in a medium containing 0.5% foetal calf serum. Some collagense digested plated were co-culture with the Elastase digest transwells at the time of initiating the starvation.

Functional modifying antibody of β1 integrin (Chemicon, clone JB1a) was added to the cultures at concentration of 1.44 and 0.48 μg/ml. The β1 integrin stimulatory antibody TS2/16 was also added at 0.9 μg/ml for 1 hour to demonstrate the specificity of the JB1a action. The β1 integrin inhibitory antibody 6S6 was also added at 1 μg/ml and 2 μg/ml for 1 hour. TGFβ neutralising antibody (R&D systems, clone 1D11) was added at a concentration of 0.1 and 0.3 μg/ml where at the lower concentration it neutralises TGFβ isoforms 1 and 3 and isoform 2 at the higher concentration. After antibody addition to the cells in culture, the medium was aspirated and the cell layer rinsed twice with ice-cold PBS (calcium- and magnesium-free). The media was aspirated and preserved after the addition of protease inhibitors at –80° C. PGs were extracted from the cell layer by extraction buffer containing protease inhibitors (4M guanidium-HCl, 4% (w/v) CHAPS, 100 mM sodium acetate buffer at pH 5.8 containing protease inhibitors) for 24 hours at 4° C.

In additional experiments, the effect of protein synthesis inhibition on β1 integrin mediated PG increase was tested by pretreating the human lung derived cells with 25 uM cycloheximide.

The effect of non-specific activation of MMPs on β1 integrin mediated PG increase was tested by pretreating the human lung derived cells with 0.5M APMA (aminophenylmercuric acetate).

To investigate the involvement of selected MMPs in initiating the response observed with β1 integrin, specific neutralising antibodies for MMP7 (1:1000, R&D systems) and MMP9 (1:1000 of clone 6-6B, Oncogene Research Products. A homophe-hydroxamic acid based broad spectrum inhibitor of MMPs was also used at 2.3 nM (MMP inhibitor III, Calbiochem).

The total protein concentration was estimated using the Bradford method.

Sample Preparation for Composite Polyacrylamide-Agarose Gel Electrophoresis

The extracts were precipitated overnight with 9 v/v ethanol at –20° C., centrifuged at 12,000 rpm for 40 minutes at 4° C. then resuspended in 0.5M sodium acetate (pH 7.3) and precipitated again with ethanol overnight and centrifuged. Samples were resuspended in 0.5% SDS and mixed with 1:1 v/v with 50% w/w sucrose in 10 mM Tris-HCl (pH 6.8), 0.5% SDS and 0.05% bromophenol blue. 20 ug of protein was used for gel loading.

Gel Electrophoresis

Composite gels (1.5 mm thick) containing 0.6% agarose and 1.2% polyacrylamide in Tris-sodium acetate buffer (10 mM, pH 6.8) containing 0.25 mM sodium sulphate were used for the separation of large PG, versican, aggrecan and perlecan, under associative conditions according to the method of Carney.

SDS-PAGE was also used to separate the denatured PG and proteins.

After electrophoretic separation, the samples were transferred onto Hybond ECL-nitrocellulose membrane (Amersham Pharmacia) using a wet blotting unit (BioRad). Membranes were blocked with 5% Milk in TBS pH 7.4 containing 0.1% v/v Tween-20 and 0.1% sodium azide for 1 hours at room temperature and then incubated with primary antibodies diluted in TBS-Tween 20 for 1 hour at room temperature or overnight at 4° C.

The primary antibody for versican (12C5) was mouse anti-human at 1/500 dilution (Hybridoma Bank, Iowa City, Iowa). This antibody recognizes the hyaluronic acid binding domain of versican (83). Aggrecan antibody was used at dilution of 1/500 aggrecan (Serotec, HAG7E1). Due to the fact that the exact epitope recognised by this antibody is unknown, additional antibodies were used. Perlcan antibody was used at a dilution of 1/1000 (7B5, Zymed Laboratories). This antibody has been demonstrated to be immunoreactive to non-degraded forms of perlecan (73). MMP1 C41-1E5), inactive MMP9 (7-11C) and TIMP1 (7-6C1) antibodies were all from Oncogene Research Products and used at 1:1000 dilution.

Some blots were stripped using 100 mM 2-mercaptoethanol, 2% SDS and 62.5 mM Tris-HCl (pH 6.7) at 56° C. for 20 minutes. They were then re-probed using a different antibody.

A horseradish peroxidase (HRP) labelled secondary antibody (goat anti mouse Ig, Dako) was added. Signal was visualised using the ECLplus (enhanced chemiluminescence) assay (Amersham Pharmacia).

The same analyses as detailed above were performed using extracts subjected to pre-clearing of the functional modifying antibodies by immunoprecipitation using protein A sepharose according to manufacturer's instructions (Amersham Pharmacia).

Immunohistochemistry (Frozen Sections)

In additional experiments, immunohistochemical staining for PG was performed on 5 um thick frozen OCT-embedded sections from human lung explants. The slides were blocked by incubating with universal blocking solution for 10 minutes at room temperature followed by biotin blocking solution for 10 minutes (Dako). Sections were then rinsed with TBS (0.5 M Tris, pH 7.6, 1.5 M NaCl), and incubated with the primary antibody. After washing with TBS, the tissue was incubated with a 1/200 biotin-labeled goat anti-mouse in TBS for 1 hour, rinsed with TBS and then further incubated with 1/100 alkaline phosphatase-conjugated avidin in TBS for 1 hour. After further washing, sections were developed with Fast Red salt 1 mg/ml in alkaline phosphatase substrate for 15 minutes at room temperature. Sections were counter-stained with Gil's Haematoxylin for 45 seconds, then washed with water.

The sections were covered with a thin layer of crystal mount and dried in the oven at 37° C., overnight.

Therapeutic Effect Using an In Vivo Animal Model of Injury: Model of Emphysema Induced by Instillation of Porcine Pancreatic Elastase Emphysema Female C57/BL6 mice (6-8 weeks old) were instilled intra-tracheally using a metal cannula with 1 IU/g body weight porcine pancreatic elastase (Roche). Mice were sampled at day 10 post instillation and histology examined to verify the presence of air space enlargement. At day 12, mice were treated intra-tracheally with the integrin antibody at 50 ug/animal in sterile PBS. Control group was instilled initially with PBS and at day 12 with isotype control IgG1 (50 ug/animal). At day 19 post elastase instillation, the animals were sacrificed, bronchoalveolar lavage fluid (BALF) collected and used to quantify the cytokines (KC (murine homologue of human IL8) and active TGFb1) using sandwich ELISA (R & D Systems).

The lungs were then removed en bloc and formalin-fixed at a pressure of 25 cm water, for histological assessment of damage and morphometric analysis (mean linear intercept). Blocks were sectioned at 5 um thickness and stained using Haematoxylin and Eosin. Sagittal sections were used from each animal. Images from 10 fields per section at 100× magnification were digitised and analysed using Scion image (NIH). Actual field size was 1.33 (H)×1.03 (V) mm. The number of alveolar walls intercepting a horizontal and a vertical line was counted. Mean linear intercept was calculated from each field (horizontal and vertical) by dividing the length of the line by the number of intercepts.

In a follow-up study, female C57/BL6 mice (6-8 weeks old) were instilled intra-tracheally using a microspray device (Penn Century, USA) with 0.2 IU/g body weight porcine pancreatic elastase (Roche). Mice were sampled at day 14 post instillation and histology examined to verify the presence of air space enlargement. At day 14 or 21, mice were treated intra-tracheally using microspray with the integrin antibody at 60 ug/animal in sterile PBS. Control group was instilled initially with PBS and at day 14 or 21 with PBS. For the group treated at day 14, the animals were terminated at day 21 as follows: The animals were anaesthetised using sodium pentobarbitone (45 mg/kg), paralysed using pancuronium bromide (0.8 mg/kg) and tracheostomised and ventilated using a small animal ventilator (Flexivent, SCIREQ, Montreal) at 8 ml/kg and a rate of 150 breaths/minute and positive end expiratory pressures (PEEP) of 3.5 cmH$_2$O in pressure limited fashion. The computer-controlled ventilator enables the measurement of pulmonary mechanics (airway resistance, tissue resistance and elasticity, pressure-volume curves) by applying an interrupter signals. For the complex impedance measurements, a signal of 8 seconds containing 19 prime sinusoidal waves with amplitude of 1.6 ml/kg between 0.5 and 19.6 Hz is applied. The signals of cylinder pressure and piston volume displacement obtained during the perturbations are low-pass filtered and stored on a computer for analysis using the constant phase model (39-41). Newtonian Resistance or airway resistance (Raw) of the Constant Phase Model represents the resistance of the central airways. Tissue damping (G) is closely related to tissue resistance and reflects the energy dissipation in the lung tissues. The parameter H is closely related to tissue elastance and reflects the energy conservation in the lung tissues.

The pressure-volume curve is obtained during inflation and deflation in a stepwise manner by applying volume perturbation incrementally during 16 seconds. The pressure signal is recorded and the pressure-volume (P-V) curve is calculated from the plateau of each step. The constant K was obtained using the Salazar-Knowles equation and reflects the curvature of the upper portion of the deflation PV curve. Quasi-static Elastance. Quasi-static elastance reflects the static elastic recoil pressure of the lungs at a given lung volume. It is obtained by calculating the slope of the linear part of P-V curve.

After the measurements, the animals were sacrificed, bronchoalveolar lavage fluid (BALF) collected. The BALF was centrifuged at 2000 rpm for 10 min and the supernatants stored at −70° C.

Histochemistry

The lungs were then removed en bloc and formalin-fixed at a pressure of 25 cm water. The lungs were paraffin-embedded and sectioned at 4 μm thickness sections. Sagittal sections were used from each animal for histological and immunohistochemical assessment of damage, and morphometric analysis (mean linear intercept, Lm).

Morphometric assessment of Lm was performed on sections deparaffinated (using xylene and absolute ethanol followed by 90% and 70% and 50% ethanol) and then stained with Haematoxylin and eosin. Images from 10 fields per section were digitised using 10× objective and the field size was 0.83 μm×0.63 μm.

Histological assessment of elastic fibre damage was performed by staining deparaffinated tissue section (using xylene and absolute ethanol followed by 90% and 70% and 50% ethanol) with Resorcin-Acid Fuschin (Elastin Products, U.S.A.) according to the manufacturer's instructions. Counter staining was performed using 0.5% tartrazine in 0.25% acetic acid. Elastic fibres appear dark red or purple and the rest of the tissue appears yellow.

Terminal Deoxyribonucleotidyl Transferase (TdT)-Mediated dUTP Nick End Labelling (TUNEL)

Tissue sections were deparaffinated using xylene and absolute ethanol followed by 90% and 70% ethanol. The sections were stained using the Red ApopTag™ Kit (Chemicon) according to the manufacturer instructions.

The principle of this technique relies on the addition of nucleosides at 3'-OH end of a piece of DNA by TdT. The enzyme in the presence of divalent cation will transfer a nucleotide to the 3'-OH end whether it is blunt, protruding or recessed. The labelling tools in TUNEL method are very versatile. The TUNEL method used for detection of apoptosis utilising TdT tagged with digoxygenin-11-dUTP and dATP was used for end-extension of 3'-OH ends of double or single stranded DNA. Rhodamine labelled anti-digoxygenin was then used for immunohistochemical staining. It is worthwhile to mention that the digoxygenin/anti-digoxygenin labelling system is preferable over the avidin/biotin system due to its lower background. The former system signal yield is also 38-fold more intense than the latter. In conjunction with TUNEL, DAPI was used as a fluorescent nuclear counterstain. Quantification of apoptotic nuclei (stained positively) is performed using confocal microscopy using ×40 objective. Images were acquired by stacking (4×4) which account for a total area of 0.921 mm×0.921 mm from a section of 8 mm×8 mm. The number of alveolar walls intercepting a horizontal and a vertical line was counted. Mean linear intercept was calculated from each field (horizontal and vertical) by dividing the length of the line by the number of intercepts.

Positive controls were also used. Sections were deparaffinated using xylene and absolute ethanol followed by 90% and 70% ethanol. Tissue sections were then subjected to DNAs treatment for 10 minutes at room temperature (2000 U/ml in 30 mM Trizma Base, pH 7.2, 4 mM MgCl$_2$, 0.1 mM DTT).

Negative controls were included were sections were incubated only with the nucleotides in the absence of the reaction enzyme.

Our experiments demonstrate a novel finding which is that that an increase in ECM PGs anabolism can be achieved via functional modification of the cell surface β1 integrin and to a much lesser extent to neutralising TGFβ in both time- and dose-dependent manner in human lung explants and human lung derived cell co-cultures as well as pulmonary derived epithelial cell line. Our experiments have demonstrated that the increase in ECM PGs was partially due to de novo protein synthesis. The changes were accompanied by an increase in TIMP1, inactivation of MMP9 and decrease in MMP1.

We have also induced emphysematous injury in the lung using porcine pancreatic elastase. Elastase induced a statistically significant two-three fold increase in the mean linear intercept (Lm) accompanied by an increase in lung size. Emphysematous mice treated by intratracheal dose of anti β1 integrin at day 12, 14 or 21 showed marked reduction in lung size at day 19-21 and 35. The change was accompanied by a significant reduction in the Lm, improvement in lung function and restoration of elastic fibres. The changes were also accompanied by a decrease in cell death. We therefore postulate that β1 integrin functional modification may have caused "loosening" of cells from the underlying damaged ECM and thus modified its mechanosensing (shock absorption) in a manner permissible for repair to ensue. This mechanism could be in addition the above mechanisms involving alteration of MMP/TIMP balance.

Furthermore, porcine pancreatic elastase resulted in a decrease in active TGFβ1 in the bronchoalveolar lavage which appeared to be reversed by the treatment. The levels of active TGFβ1 exhibited a statistically significant correlation ($r=0.96$, $p<0.01$) with the Lm.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES

The subject matter of the following publications is incorporated herein by reference.

REFERENCE LIST

1. Albuquerque M L and Flozak A S. *J Cell Physiol* 195: 50-60, 2003.
2. Aspberg A et al. *J Biol Chem* 274: 20444-20449, 1999.
3. Aspberg A et al. *Proc Natl Acad Sci USA* 94: 10116-10121, 1997.
4. Aumailley M and Gayraud B. *J Mol Med* 76: 253-265, 1998.
5. Aviezer D et al. *Cell* 79: 1005-1013, 1994.
6. Badger A M et al, *Arthritis Rheum* 44: 128-137, 2001.
7. Bang O S et al. *Biochem Biophys Res Commun* 278: 522-529, 2000.
8. Barnes P J. *Annu Rev Med* 54: 113-129, 2003.
9. Bensadoun E S, Burke A K, Hogg J C and Roberts C R. Proteoglycan deposition in pulmonary fibrosis. *Am J Respir Crit Care Med* 154: 1819-1828, 1996.
10. Bingley J A et al. *J Vasc Surg* 28: 308-318, 1998.
11. Bird R E et al. *Science* 242: 423-426, 1988.
12. Bozzo C et al. *Mol Cell Neurosci* 25: 1-8, 2004.
13. Brown C T et al. *J Biol Chem* 274: 7111-7119, 1999.
14. Brown J C et al. *Eur J Biochem* 250: 39-46, 1997.
15. Calverley P and Bellamy D. *Thorax* 55: 78-82, 2000.
16. Cao L et al. *Matrix Biol* 18: 343-355, 1999.
17. Cawston T et al. *Novartis Found Symp* 234: 205-218, 2001.
18. Chakravarti S et al. *J Biol Chem* 270: 404-409, 1995.
19. Costell M et al. *J Cell Biol* 147: 1109-1122, 1999.
20. Couchman J R et al. *Kidney Int* 43: 79-84, 1993.
21. Curley G P et al. *Cell Mol Life Sci* 56: 427-441, 1999.
22. Dolhnikoff M et al. *Am J Respir Cell Mol Biol* 19: 582-587, 1998.
23. Dunlevy J R and Hassell J R. Heparan Sulfate Proteoglycans in Basement Membranes: Perlecan, Agrin, and Collagen XVIII. In: Proteoglycans: Structure, Biology and Molecular Interactions, edited by Iozzo R V. New York: Marcel Dekker, 2000, p. 275-326.
24. Ebihara T et al., Venkatesan N, Tanaka R and Ludwig M S. *Am J Respir Crit Care Med* 162: 1569-1576, 2000.
25. Elbert K J et al. *Pharm Res* 16: 601-608, 1999.
26. Ettner N et al. *FEBS Lett* 430: 217-221, 1998.
27. Evanko S P et al. *Arterioscler Thromb Vasc Biol* 19: 1004-1013, 1999.
28. Festuccia C et al. *Exp Cell Res* 280: 1-11, 2002.
29. Freedman G M. *Geriatrics* 57: 36-41, 2002.
30. Fuki I V et al. *J Biol Chem* 275: 25742-25750, 2000.
31. Gallagher J T. *Biochem Soc Trans* 25: 1206-1209, 1997.
32. Goldsmith E C et al. *Am J Physiol Heart Circ Physiol* 284: H2227-H2234, 2003.
33. Goodison S et al. *Mol Pathol* 52: 189-196, 1999.
34. Green S J et al. *J Cell Sci* 90 (Pt 1): 145-156, 1988.
35. Green S J and Underhill C B. *J Cell Physiol* 134: 376-386, 1988.
36. Groffen A J et al *Eur J Biochem* 254: 123-128, 1998.
37. Grose R et al. *Development* 129: 2303-2315, 2002.
38. Halfter W et al. *J Biol Chem* 273: 25404-25412, 1998.
39. Hantos Z et al. *J Appl Physiol* 73: 427-433, 1992.
40. Hantos Z et al. *J Appl Physiol* 68: 849-860, 1990.
41. Hantos Z et al. *J Appl Physiol* 72: 168-178, 1992.
42. Haralson M A and Hassell J R. The extracellular matrix—an overview. In: Extracellular Matrix: A practical approach, edited by Haralson M A and Hassell J R. Oxford University Press, 1995, p. 1-30.
43. Hartwell L H et al. *Nature* 402: C47-052, 1999.
44. Hassell J R et al. *Proc Natl Acad Sci USA* 77: 4494-4498, 1980.
45. Hirose J et al. *J Biol Chem* 2000.
46. Hollinger M. Flight to duty. *Am J Nurs* 101: 15, 2001.
47. Hopf M et al. *Eur J Biochem* 259: 917-925, 1999.
48. Humphries M J. *J Cell Sci* 97 (Pt 4): 585-592, 1990.
49. Humphries M J. *Trends Pharmacol Sci* 21: 29-32, 2000.
50. Huston J S et al. *Proc Natl Acad Sci USA* 85: 5879-5883, 1988.
51. Iozzo R V. *Matrix Biol* 14: 203-208, 1994.
52. Iozzo R V. *Annu Rev Biochem* 67: 609-652, 1998.
53. Jackson R L et al. *Physiol Rev* 71: 481-539, 1991.
54. Juul S E et al. *Am J Respir Cell Mol Biol* 8: 299-310, 1993.
55. Kawashima H et al. *J Biol Chem* 275: 35448-35456, 2000.
56. Kawashima H et al. *Int Immunol* 11: 393-405, 1999.
57. Kennel S J et al. *J Cell Sci* 104 (Pt 2): 373-382, 1993.
58. Knight D. *Immunol Cell Biol* 79: 160-164, 2001.

59. Koenig A et al. *J Clin Invest* 101: 877-889, 1998.
60. Kraneveld A D et al. *J Allergy Clin Immunol* 100: 242-250, 1997.
61. Lebaron R G et al. *J Biol Chem* 267: 10003-10010, 1992.
62. Leir S H et al. *Am J Physiol Lung Cell Mol Physiol* 278: L1129-L1137, 2000.
63. Lemire I M et al. *Arterioscler Thromb Vasc Biol* 19: 1630-1639, 1999.
64. Levkau B et al. *Cell Death Differ* 9: 1360-1367, 2002.
65. Li Y F et al. *FEBS Lett* 444: 201-205, 1999.
66. Little C B et al. *Matrix Biol* 21: 271-288, 2002.
67. Loftus I M et al. *Br J Surg* 89: 680-694, 2002.
68. Maniotis A J et al. *Proc Natl Acad Sci USA* 94: 849-854, 1997.
69. Maniscalco W M and Campbell M H. *Am J Physiol* 263: L348-L356, 1992.
70. Mengshol J A et al. *Arthritis Rheum* 46: 13-20, 2002.
71. Milne A A and Piper P J. *Eur J Pharmacol* 282: 243-249, 1995.
72. Mould A P et al. *J Biol Chem* 2003.
73. Murdoch A D et al. *J Histochem Cytochem* 42: 239-249, 1994.
74. Murdoch A D et al. *J Histochem Cytochem* 42: 239-249, 1994.
75. Murphy S A et al. *Methods Cell Sci* 21: 31-38, 1999.
76. Nakayamada S et al. *J Biol Chem* 278: 45368-45374, 2003.
93. Toole B P. *Curr Opin Cell Biol* 2: 839-844, 1990.
94. Tuckwell D S and Humphries M J. *Crit Rev Oncol Hematol* 15: 149-171, 1993.
95. Turato G, Zuin R and Saetta M. *Respiration* 68: 117-128, 2001.
96. Turino G M. *Am Rev Respir Dis* 132: 1324-1334, 1985.
97. van Kuppevelt T H et al. *Eur J Cell Biol* 36: 74-80, 1985.
98. Villar M J et al. *J Cell Biochem* 75: 665-674, 1999.
99. Ward E S et al. *Nature* 341: 544-546, 1989.
100. Watanabe H et al. *J Biochem* (Tokyo) 124: 687-693, 1998.
101. Wernig F et al. *Hypertension* 41: 903-911, 2003.
102. Westergren-Thorsson G et al. *J Clin Invest* 92: 632-637, 1993.
103. Wirtz H R and Dobbs. L G. *Respir Physiol* 119: 1-17, 2000.
104. Yamagata M et al. *J Cell Sci* 106 (Pt 1): 55-65, 1993.
105. Zako M et al. *J Biol Chem* 272: 9325-9331, 1997.
106. Zako M et al. *J Biol Chem* 270: 3914-3918, 1995.
107. Zhang Y et al. *J Cell Biochem* 73: 445-457, 1999.
108. Zhang Y et al. *J Biol Chem* 273: 21342-21351, 1998.
109. Zimmermann D R. Versican. In: Proteoglycans: Structure, Biology and Molecular Interactions, edited by Iozzo R V. New York: Marcel Dekker, 2000, p. 327-342.
110. Zimmermann D R and Ruoslahti E. *EMBO J* 8: 2975-2981, 1989.
111. Zou K et al. *Eur J Biochem* 267: 4046-4053, 2000.

SEQUENCE LISTING

```
<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Thr Ala Glu Lys Leu Lys
1               5
```

77. Nakayamada S et al. *Arthritis Rheum* 48: 1239-1248, 2003.
78. Newsome P N et al. *Hepatology* 40: 636-645, 2004.
79. Noonan D M et al. *J Biol Chem* 266: 22939-22947, 1991.
80. Norgard-Sumnicht K and Varki A. *J Biol Chem* 270: 12012-12024, 1995.
81. Otterness I G et al. *Arthritis Rheum* 41: 2068-2076, 1998.
82. Paulus W et al. *J Neuropathol Exp Neurol* 55: 528-533, 1996.
83. Perides G et al. *J Biol Chem* 267: 23883-23887, 1992.
84. Poole A R et al. *Agents Actions Suppl* 39: 3-13, 1993.
85. Roberts C R. Proteoglycans. In: The Lung: Scientific Foundations, edited by barnes pj, grunstein mm, leff ar and woolcock aj. Philadeliphia: Lippincott-Raven Publishers, 1997, p. 757-767.
86. Shapiro S D. *Biochem Soc Trans* 30: 98-102, 2002.
87. Sharma B et al. *J Clin Invest* 102: 1599-1608, 1998.
88. Shinomura T et al. *J Biol Chem* 268: 14461-14469, 1993.
89. Spicer A P and McDonald J A. 1999 Eukaryotic Hyaluronan Synthases [Online]. Seikagaku Japan, 1999.
90. Sun M et al. *Circulation* 107: 1046-1052, 2003.
91. Takahashi I et al. *J Cell Sci* 111 (Pt 14): 2067-2076, 1998.
92. Thickett D R et al. *Sarcoidosis Vasc Diffuse Lung Dis* 18: 27-33, 2001.

The invention claimed is:

1. A method of enhancing tissue repair and regeneration to treat emphysema comprising administering an antibody, or an antigen binding fragment thereof, which modulates function of beta 1 integrin to a subject in need thereof, wherein the antibody or an antigen binding fragment binds to a domain of beta 1 integrin comprising amino acid residues 82 to 87 comprising residues TAEKLK (SEQ ID NO: 1) of mature beta 1 integrin and wherein the functional modulation of beta 1 integrin results in (i) an inhibition of apoptotic pathway, (ii) an alteration in metalloproteinases, (iii) an increase in an anabolism of extracellular matrix and (iv) an increase in inactive-MMP9.

2. The method according to claim 1, wherein the antibody is a monoclonal antibody produced by commercial clone JB1a.

3. The method of claim 1, wherein the antibody is selected from the group consisting of a humanized antibody, a chimeric antibody and a human antibody.

4. The method of claim 1, wherein the antibody is a fragment of a monoclonal antibody produced by commercial clone JB1a.

5. The method of claim 1, wherein the functional modulation causes shedding of beta 1 integrin.

6. The method of claim 1, wherein the functional modulation includes an increase in TIMP1.

7. The method of claim 1, wherein administering the antibody or antigen binding fragment reverses an abnormal increase in mean linear intercept as an index of air space enhancement, lung size and abnormal lung function.

8. The method of claim 1, wherein the method increases cell viability.

9. A method of enhancing tissue repair and regeneration to treat emphysema comprising administering an antibody, or an antigen binding fragment thereof, which modulates function of beta 1 integrin to a subject in need thereof, wherein the antibody or antigen binding fragment binds to beta 1 integrin in a region of amino acid residues 82 to 87 comprising residues TAEKLK (SEQ ID NO:1) of mature beta 1 integrin and wherein the functional modulation of beta 1 integrin results in (i) an inhibition of apoptotic pathway, (ii) an alteration in metalloproteinases, (iii) an increase in an anabolism of extracellular matrix and (iv) an increase in inactive-MMP9.

* * * * *